US011471383B2

(12) United States Patent
Debeaud et al.

(10) Patent No.: US 11,471,383 B2
(45) Date of Patent: Oct. 18, 2022

(54) LIP COMPOSITION IN THE FORM OF A LIQUID INVERSE EMULSION

(71) Applicant: L'OREAL, Paris (FR)

(72) Inventors: Roshanak Debeaud, Chevilly Larue (FR); Régine Imbert, Chevilly Larue (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/467,761

(22) PCT Filed: Dec. 21, 2017

(86) PCT No.: PCT/EP2017/084241
§ 371 (c)(1),
(2) Date: Jun. 7, 2019

(87) PCT Pub. No.: WO2018/115366
PCT Pub. Date: Jun. 28, 2018

(65) Prior Publication Data
US 2020/0069542 A1 Mar. 5, 2020

(30) Foreign Application Priority Data
Dec. 21, 2016 (FR) ..................... 16 63033

(51) Int. Cl.
A61K 8/06 (2006.01)
A61K 8/31 (2006.01)
A61K 8/34 (2006.01)
A61K 8/73 (2006.01)
A61K 8/81 (2006.01)
A61K 8/891 (2006.01)
A61K 8/92 (2006.01)
A61Q 1/04 (2006.01)

(52) U.S. Cl.
CPC ............... *A61K 8/064* (2013.01); *A61K 8/31* (2013.01); *A61K 8/342* (2013.01); *A61K 8/731* (2013.01); *A61K 8/8111* (2013.01); *A61K 8/891* (2013.01); *A61K 8/927* (2013.01); *A61Q 1/04* (2013.01); *A61K 2800/40* (2013.01)

(58) Field of Classification Search
None
See application file for complete search history.

(56) References Cited

U.S. PATENT DOCUMENTS

| 4,948,584 A | 8/1990 | Brand |
| 5,908,631 A | 6/1999 | Arnaud et al. |
| 6,503,516 B1 | 1/2003 | Van Liew et al. |
| 8,894,982 B2 | 11/2014 | Susak et al. |
| 2016/0310374 A1 | 10/2016 | Debeaud et al. |

FOREIGN PATENT DOCUMENTS

| FR | 3 015 277 A1 | 6/2015 |
| WO | WO 2014158599 | * 10/2014 |
| WO | WO 2015/097185 A1 | 7/2015 |

OTHER PUBLICATIONS

Database GNPD Mintel, "Lip & Contour Double Care", Sep. 1, 2010; XP-002769559.
Database GNPD Mintel, "Moisture Lip Balm", Nov. 1, 2013; XP-002769560.

* cited by examiner

*Primary Examiner* — Tigabu Kassa
(74) *Attorney, Agent, or Firm* — Polsinelli PC

(57) ABSTRACT

This invention relates to a composition, in the form of a water-in-oil emulsion, containing: —at least 6% by weight in relation to the total weight of the composition, of at least one non-volatile hydrocarbon-based oil H1 chosen from plant oils or non-volatile triglycerides with a molecular weight greater than 400 Da, non-volatile non-polar hydrocarbon-based oils with a molecular weight greater than 350 Da, non-volatile ester oils with a molecular weight greater than 350 Da, and mixtures thereof; —optionally less than 5% by weight in relation to the total weight of said composition of non-volatile hydrocarbon-based oil(s) H2 chosen from $C_{10}$-$C_{26}$ alcohols, preferably monoalcohols; non-volatile triglycerides with a molecular weight less than or equal to 400 Da; non-volatile ester in oils with a molecular weight less than or equal to 350 Da; non-volatile non-polar hydrocarbon-based oils with a molecular weight less than or equal to 350 Da; dialkyl carbonates; and mixtures thereof; —at least 15% by weight of water with respect to the total weight of said composition; —at least one nonionic hydrocarbon-based or silicone surfactant; and —at least one polar hydrocarbon-based wax chosen from beeswaxes; synthetic beeswaxes; (poly)oxyalkylenated hydrocarbon waxes, the oxyalkykenated residue(s) being $C_2$-$C_4$ or (poly)glycerolated; alcohol waxes, and mixtures thereof.

21 Claims, No Drawings

LIP COMPOSITION IN THE FORM OF A LIQUID INVERSE EMULSION

CROSS REFERENCE TO RELATED APPLICATIONS

This application is a National Phase filing under 35 U.S.C. § 371 of PCT/EP2017/084241 filed on 21 Dec. 2017; which application in turn claims priority to Application No. 16 63033 filed in France on 21 Dec. 2016. The entire contents of each application are hereby incorporated by reference.

This invention concerns a composition, intended to be applied on the lips, in the form of a liquid inverse emulsion.

It also concerns a treatment method for lips by application on the lips of said composition.

Moisturizing compositions, colored or not, for example lip balms or serums, are commonly used. In this respect, a wide diversity of formulations, solid or liquid, have already been developed.

In particular, there are today interesting conventional compositions for moisturizing lips, and/or in particular dry and chapped lips. They act more particularly by forming an occlusive barrier on their surface which helps maintain the water in the lips, in order to improve their sensory properties (softness, etc.).

However, this action mode is not long lasting. In particular, the moisturizing effect associated with such compositions does not persist over time, and clearly decreases as soon as the composition is no longer applied on the lips. Consequently, regular and repeated applications are required from the user.

For obvious reasons, it would be advantageous to be able to not be subject to these repeated applications.

Furthermore, even if the fact of feeling the presence of the deposit of these compositions on the lips can be associated by the users with a barrier action against outside aggressions, the fact remains that in certain cases, this deposit can be perceived as too heavy, too greasy, even tacky.

Finally, it was able to be observed that for compositions that have the form of an emulsion, that in certain cases, the application of the composition was not done easily, resulting in the obtaining of a non-homogeneous deposit, in color and in thickness. It was indeed possible to feel a substantial sliding effect without feeling a deposit of the composition (it is said that the application "chases"), with this effect able to be accompanied by a "soaping" effect of the composition on the lips, resulting in the appearance either of a white coloration of the lips, or of a less intense coloration of the deposit if the composition contains pigments.

There is thus still a genuine need to have compositions that are easy to apply, able to guarantee the user a comfortable sensory feeling, not only with regards to the deposit itself, on the lips (light, little or not greasy, at hardly tacky) but also in terms of flexibility and moisturizing of the lips over a prolonged period even after the stopping of the application of the composition.

In this way, this invention relates to a composition, in the form of a water-in-oil emulsion, containing:

- at least 6% by weight in relation to the total weight of the composition, of at least one non-volatile hydrocarbon-based oil H1 chosen from plant oils or non-volatile triglycerides with a molecular weight greater than 400 Da, non-volatile non-polar hydrocarbon-based oils with a molecular weight greater than 350 Da, non-volatile ester oils with a molecular weight greater than 350 Da, and mixtures thereof;
- optionally less than 5% by weight in relation to the total weight of said composition of non-volatile hydrocarbon-based oil(s) H2 chosen from $C_{10}$-$C_{26}$ alcohols, preferably monoalcohols; non-volatile triglycerides with a molecular weight less than or equal to 400 Da; non-volatile ester oils with a molecular weight less than or equal to 350 Da; non-volatile non-polar hydrocarbon-based oils with a molecular weight less than or equal to 350 Da; dialkyl carbonates; and mixtures thereof;
- at least 15% by weight, preferably at least 20%, of water with respect to the total weight of said composition;
- at least one nonionic hydrocarbon-based or silicone surfactant; and
- at least one polar hydrocarbon-based wax chosen from beeswaxes; synthetic beeswaxes; (poly)oxyalkylenated hydrocarbon-based waxes, the oxyalkykenated residue(s) being $C_2$-$C_4$ or (poly)glycerolated; alcohol waxes, and mixtures thereof.

Another object of the invention is represented by a method of treatment and/or of makeup of human keratin matter, in particular lips, in which the aforementioned composition is applied.

It was surprisingly observed that the effect of improving the flexibility of the lips and the feeling of hydration, remained perceptible several days after the stopping of the applying of the composition according to the invention.

In addition, the composition according to the invention is easy to apply and leaves a light, non-greasy deposit which is not tacky.

The composition according to the invention is moreover easy to apply in particular it does not "chase", and makes it possible to obtain a homogeneous deposit, for which the soaping phenomenon is practically non-existent.

But other advantages of the invention will be apparent when reading the non-limiting description and examples that shall follow.

The expression "between" or "ranging from" must be understood as including the limits.

The composition according to the invention is cosmetic and advantageously includes a physiologically acceptable medium, i.e. a medium that is particularly suitable for the application of a composition of the invention on the lips.

The physiologically acceptable medium is generally suitable for the nature of the support to which the composition should be applied, and also for the way in which the composition is to be packaged.

Preferably, the composition is in liquid form or in the form of a cream or a butter or a paste.

The viscosity at 20° C. is more particularly greater than or equal to 20 Pa·s. Preferably, it has a viscosity between 20 and 100 Pa·s, preferably between 30 and 80 Pa·s.

According to another particular embodiment, the viscosity at 25° C. is more particularly greater than or equal to 2 Pa·s. Preferably, it has a viscosity between 2 and 10 Pa·s, preferably between 3 and 8 Pa·s.

Note that the terms paste or butter mean a composition that is not solid, and of which it is possible to measure the viscosity.

Protocol for Measuring Viscosity:

The viscosity is measured at 25° C., using a RHEOMAT RM 180 viscometer equipped with a moving body no. 3 or 4, the measurement being made after 10 minutes of rotation of the moving body (time after which stabilization of the viscosity and rotational speed of the moving body is observed), at a shear rate of 200 $s^{-1}$.

Non-Volatile H1 Hydrocarbon-Based Oils

The term "oil" is intended to mean in this invention a compound that is liquid at 25° C. and at atmospheric pressure ($1.013.10^5$ Pa).

"Non-volatile" refers to a compound of which the vapor pressure at ambient temperature (25° C.) and atmospheric pressure, is not zero and less than 0.02 mm of Hg (2.66 Pa), preferably less than $10^{-3}$ mm of Hg (0.13 Pa).

By way of example, the vapor pressure may be measured according to the static method. The vapor pressure may also be measured according to the method of effusion by isothermal thermogravimetry (OECD Guideline 104).

As such, the compositions according to the invention can comprise one or more non-volatile plant oils or triglycerides with a molecular weight greater than 400 Da, non-volatile non-polar hydrocarbon-based oils with a molecular weight greater than 350 Da, and/or one or several non-volatile ester oils with a molecular weight greater than 350 Da, as well as mixtures thereof.

Plant Oils or Non-Volatile Triglycerides with a Molecular Weight Greater than 400 Da According to the invention, the non-volatile plant oil or the triglyceride having a molecular weight greater than 400 Da, can be chosen from:
- triglycerides of fatty acids in $C_7$-$C_{40}$, in particular saturated, such as triglycerides of heptanoic or octanoic acids, triglycerides of caprylic/capric acid and mixtures thereof, and triglycerides of acids in $C_{18}$-$C_{36}$;
- saturated or unsaturated plant hydrocarbon-based oils, such as jojoba oil, castor oil, olive oil, coconut oil, DHA algal oil, ximenia oil, pracaxi oil, coriander seed oil, macadamia oil, passionflower oil, argan oil, sesame oil, sunflower oil, grape seed oil, avocado oil, rosa canina oil, apricot kernel oil, flax oil, sweet almond oil, cotton seed oil, soybean oil, rapeseed oil, groundnut oil, kaya oil, the liquid shea butter fraction, and the liquid cocoa butter fraction; and/or
- mixtures thereof.

Non-Volatile Non-Polar Hydrocarbon-Based Oils with a Molecular Weight Greater than 350 Da The non-volatile non-polar hydrocarbon-based oils according to this invention may be of plant, mineral or synthetic origin.

The term "non-polar oil", within this invention, refers to an oil that comprises carbon and hydrogen atoms. A non-polar hydrocarbon-based oil, within the invention, is therefore devoid of other atoms, in particular oxygen, nitrogen, silicon or fluorine atoms.

Preferably, the non-volatile non-polar hydrocarbon-based oil may be chosen from mineral or synthetic linear or branched hydrocarbons such as, for example:
- squalane;
- polybutenes such as for example INDOPOL H-100 (having a molecular weight of MW=965 g/mol), INDOPOL H-300 (MW=1,340 g/mol), INDOPOL H-1500 (MW=2,160 g/mol) sold or manufactured by AMOCO;
- polyisobutenes, hydrogenated or not, such as for example Parleam V® sold by NIPPON OIL FATS, PANALANE H-300 E sold or manufactured by AMOCO (MW=1340 g/mol), VISEAL 20000 sold or manufactured by SYNTEAL (MW=6,000 g/mol), REWOPAL PIB 1000 sold or manufactured by WITCO (MW=1,000 g/mol);
- decene/butene copolymers, polybutene/polyisobutene copolymers, particularly INDOPOL L-14;
- polydecenes and hydrogenated polydecenes such as in particular: PURESYN 10 (MW=723 g/mol), PURESYN 150 (MW=9,200 g/mol) sold or manufactured by MOBIL CHEMICALS, or PURESYN 6 sold by EXXONMOBIL CHEMICAL; and
- mixtures thereof.

According to a preferred embodiment, the non-volatile non-polar hydrocarbon-based oil having a molecular weight greater than 350 Da is chosen from polybutenes hydrogenated or not, polyisobutenes hydrogenated or not, polydecenes hydrogenated or not, squalane, decene/butene copolymers, polybutene/polyisobutene copolymers, and mixtures thereof.

Non-Volatile Ester Oils with a Molecular Weight Greater than 350 Da

The non-volatile ester oil with a molecular weight greater than 350 Da, can be chosen from mono-, di- or tri-esters, possibly hydroxylated, saturated, unsaturated or aromatic, comprising at least 20 carbon atoms and more particularly between 20 and 70 carbon atoms, such as for example, monoesters comprising at least 20 carbon atoms and more particularly having between 20 and 40 carbon atoms in total, in particular monoesters, having formula $R_1COOR_2$ wherein $R_1$ is the remainder of a linear or branched or aromatic fatty acid comprising from 4 to 40 carbon atoms, saturated or not, and $R_2$ is a hydrocarbon chain in particular branched containing from 4 to 40 carbon atoms provided that the sum of the carbon atoms of the $R_1$ and $R_2$ radicals is greater than or equal to 20, such as for example cetostearyl octanoate, 2-ethyl hexyl palmitate, octyldodecyl neopentanoate, isostearyl neopentanoate, octyl-2-dodecyl stearate, octyl-2-dodecyl erucate, isostearyl isostearate, octyl-2 dodecyl benzoate, butyl stearate, isocetyl stearate, 2-ethyl hexyl palmitate, 2-hexyl decyl laurate, 2-octyldodecyl palmitate, 2-octyldodecyl myristate, isocetyl palmitate, isodecyl palmitate or ethyl-hexyl iso-palmitate.

Preferably, these are esters having formula $R_1COOR_2$ wherein $R_1$ is the remainder of a linear or branched fatty acid comprising from 4 to 40 carbon atoms and $R_2$ is a hydrocarbon chain in particular branched containing from 4 to 40 carbon atoms, with $R_1$ and $R_2$ being such that the sum of the carbon atoms of the $R_1$ and $R_2$ radicals is greater than or equal to 20.

More particularly, the ester comprises between 20 and 40 carbon atoms in total.

As preferred monoesters, mention can be made of isocetylstearate, oleyl erucate and/or octyl-2-docecyl neopentanoate.

The non-volatile ester oil with a molecular weight greater than 350 Da, can be chosen from:
- fatty acid monoesters, in particular having at least 18 carbon atoms and even more particularly from 18 to 22 carbon atoms, and in particular lanolic acid, oleic acid, lauric acid, stearic acid, and diols, in particular diols in $C_2$-$C_5$;
- diesters, in particular having at least 20 carbon atoms and even more particularly comprising between 20 and 60 carbon atoms in total, in particular between 20 and 50 carbon atoms in total, such as diesters of carboxylic diacid and of monoalcohols, such as preferably diisostearyl malate, diethyl-2 hexyl adipate, or diesters of glycol and of monocarboxylic acids, such as propylene glycol dioctanoate, diethylene glycol diisononanoate, or polyglyceryl-2 diisostearate;
- hydroxylated monoesters, diesters and triesters, preferably having a total number of carbon atoms of at least 18 carbon atoms, more advantageously at least 20 and even more particularly ranging from 20 to 70, such as tributyl citrate, trioctyl citrate, acetyl tributyl citrate, polyglyceryl-3 diisostearate, octylhydroxystearate, octyldodecyle hydroxystearate, diisostearyl malate, glycerin stearate or glycerin palmitate;

triesters, in particular having at least 35 carbon atoms and even more particularly comprising between 35 and 70 carbon atoms in total, in particular such as triesters of carboxylic triacid, such as triisostearyl citrate, or tridecyl trimellitate, or triesters of glycol and of monocarboxylic acids such as polyglyceryl-2 triisostearate;

tetraesters, in particular having at least 35 carbon atoms and even more particularly having a total number of carbon atoms ranging from 35 to 70, such as tetraesters of penthaerythritol or of polyglycerol and of a monocarboxylic acid, such as pentaerythrityl tetrapelargonate, pentaerythrityl, tetraisostearate, tetraisononanoate pentaerythrityl, glyceryl tri decyl-2 tetradecanoate, polyglyceryl-2 tetraisostearate or pentaerythrityl tetra decyl-2 tetradecanoate;

polyesters obtained by condensing unsaturated fatty acid dimers and/or trimers and $C_3$-$C_4$ diol such as those described in particular in the patent application FR 0 853 634, such as in particular dilinoleic acid and 1,4-butanediol. Mention may particularly be made in this respect of the polymer sold by Biosynthesis under the name Viscoplast 14436H (INCI name: dilinoleic acid/butanediol copolymer), or polyol and diacid dimer copolymers, and esters thereof, such as Hailuscent ISDA;

esters and polyesters of dimer diol comprising at least 16 carbon atoms and of esters of monocarboxylic acid in $C_8$-$C_{34}$, preferably unsaturated, or a dimer of the latter; such as dimer diol and fatty acid and esters of dimer diol and carboxylic diacid dimers, in particular able to be obtained from a carboxylic diacid dimer particularly derived from the dimerization of an unsaturated fatty acid, particularly in $C_8$ to $C_{34}$, particularly in $C_{12}$ to $C_{22}$, particularly in $C_{16}$ to $C_{20}$, and more particularly in $C_{18}$, such as dilinoleic diacid esters and dilinoleic diol dimers, for example such as those sold by NIPPON FINE CHEMICAL under the trade name LUSPLAN DD-DA5® and DD-DA7®;

polyesters resulting from the esterification of at least one triglyceride of carboxylic acid(s) hydroxylated by an aliphatic monocarboxylic acid and by an aliphatic dicarboxylic acid, possibly unsaturated such as castor oil of succinic acid and of isostearic acid; and/or;

mixtures thereof.

According to an embodiment, the compositions according to the invention comprise at least one hydrocarbon-based plant oil such as defined hereinabove, preferably at least two hydrocarbon-based plant oils such as defined hereinabove, and optionally at least one non-volatile non-polar hydrocarbon-based oil chosen from linear or branched hydrocarbons.

Preferably, in the compositions according to the invention, the non-volatile hydrocarbon-based oil(s) H1 content ranges from 6% to 40% by weight, preferentially from 8% to 30% by weight, with respect to the total weight of said composition.

Non-Volatile Hydrocarbon-Based Oils H2

The compositions according to the invention can furthermore comprise one or several hydrocarbon-based non-volatile oil(s) H2 chosen from $C_{10}$-$C_{26}$ alcohols, preferably monoalcohols; non-volatile ester oils with a molecular weight less than or equal to 350 Da; non-volatile triglycerides with a molecular weight less than or equal to 400 Da; non-volatile non-polar hydrocarbon-based oils with a molecular weight less than or equal to 350 Da; dialkyl carbonates; and mixtures thereof.

Preferably, the non-volatile hydrocarbon-based oil(s) H2 chosen from $C_{10}$-$C_{26}$ monoalcohols, non-volatile triglycerides with a molecular weight less than or equal to 400 Da; non-volatile ester oils with a molecular weight less than or equal to 350 Da; non-volatile non-polar hydrocarbon-based oils with a molecular weight less than or equal to 350 Da.

According to the invention, if the composition contains any, the maximum content in oil(s) H2 does not exceed 5% by weight in relation to the total weight of said composition.

Preferably, in the compositions according to the invention, the oil(s) H2 content is less than 3%, preferably less than 1% by weight, with respect to the total weight of said composition.

The non-volatile polar or non-polar hydrocarbon-based oil H2 can be chosen from the following oils:

$C_{10}$-$C_{26}$ alcohols, preferably monoalcohols:

More particularly, the $C_{10}$-$C_{26}$ alcohols are saturated or not, branched or not, and comprise from 10 to 26 carbon atoms. Preferably, they contain from 10 to 24 carbon atoms, and more preferably from 12 to 22 carbon atoms.

Preferably, the alcohols are branched when they contain at least 16 carbon atoms.

As particular examples of fatty alcohols that can be used preferably, mention can be made in particular of lauric alcohol, isostearyl alcohol, oleic alcohol, 2-butyloctanol, 2-undecyl pentadecanol, 2-hexyldecylic alcohol, isocetylic alcohol, octyldodecanol and mixtures thereof.

non-volatile triglycerides with a molecular weight less than or equal to 400 Da such as triacetine.

ester oils chosen from:

optionally hydroxylated monoesters of a $C_2$-$C_8$ carboxylic and of a $C_2$-$C_8$ alcohol, the diesters of a $C_2$-$C_8$ carboxylic diacid and of a $C_2$-$C_8$ alcohol, optionally hydroxylated; such as diisopropyl adipate, dibutyl adipate, or 2-diethyl-hexyl succinate, the triesters of a $C_2$-$C_8$ carboxylic triacid and of a $C_2$-$C_8$ alcohol, optionally hydroxylated, such as the esters of citric acid, such as triethylcitrate, the esters of a $C_2$-$C_8$ polyol and of one or several $C_2$-$C_8$ carboxylic acids, such as the diesters of glycol and of monoacids, such as in particular neopentylglycol diheptanoate, monoesters comprising at least 17 carbon atoms and more particularly having between 17 and 25 carbon atoms in total, in particular monoesters, having formula $R_1COOR_2$ wherein $R_1$ is the remainder of a linear or branched or aromatic fatty acid comprising from 4 to 20 carbon atoms, saturated or not, and $R_2$ is a hydrocarbon chain in particular branched containing from 4 to 20 carbon atoms provided that the sum of the carbon atoms of the $R_1$ and $R_2$ radicals is greater than or equal to 17, such as for example isononyl isononanoate, $C_{12}$-$C_{15}$ alkyl benzoates, isopropyl myristate, isopropyl palmitate, butyl stearate or hexyl laurate, fatty acid monoesters, in particular having at least 18 carbon atoms and even more particularly from 18 to 22 carbon atoms, and in particular lanolic acid, oleic acid, lauric acid, stearic acid, and diols, such as propylene glycol monoisostearate, hydroxylated monoesters and diesters, preferably having a total number of carbon of at least 18 carbon atoms and even more particularly ranging from 18 to 25, such as isostearyl lactate, dialkyl carbonates, the 2 alkyl chains possibly being identical or different, such as the dicaprylyl carbonate sold under the name Cetiol CC®, by Cognis.

and mixtures thereof.

Wax(es)

The compositions according to the invention comprise at least one polar hydrocarbon-based wax such as defined above. They may comprise a mixture of a plurality of waxes.

Generally, a wax considered in the framework of this invention is a lipophilic compound, which is solid at ambient temperature (25° C.), having a reversible solid/liquid change of state and a melting point greater than or equal to 30° C. of up to 200° C. and particularly up to 120° C.

The melting point of a wax can be measured using a differential scanning calorimeter (DSC), for example the calorimeter sold under the trade name "DSC Q100" by TA Instruments with the "TA Universal Analysis" software.

According to the invention, the melting temperature corresponds more particularly to the temperature of the most endothermic peak observed in DSC as described in the norm ISO 11357-3; 1999.

The measurement protocol can be as follows:

A sample of solid fat (wax) of about 5 mg is placed in a "sealed aluminum capsule" crucible.

When the solid fat is hard (wax), the sample is subjected to a first temperature rise from 20° C. to 120° C., at a heating rate of 2° C./minute, and to 80° C., then left at isotherm of 100° C. for 20 minutes, then is cooled from 120° C. to 0° C. at a cooling rate of 2° C./minute, and finally subjected to a second temperature rise from 0° C. to 20° C. at a heating rate of 2° C./minute.

The value of the melting temperature of the solid fat (wax) is the value of the top of the most endothermic peak of the fusion curve observed, representing the variation in the difference in power absorbed as a function of the temperature.

The wax or waxes that are suitable for carrying out this invention are therefore chosen from beeswax; synthetic beeswaxes; (poly)oxyalkylenated hydrocarbon-based waxes, with the oxyalkykenated residue(s) being in $C_2$-$C_4$ or (poly)glycerolated; alcohol waxes, and mixtures thereof. Preferably, the wax or waxes (is)are chosen from beeswax; synthetic beeswaxes; (poly)oxyalkylenated hydrocarbon-based waxes, with the oxyalkykenated residue(s) being in $C_2$-$C_4$ or (poly)glycerolated, and mixtures thereof.

With regards to beeswax, mention can be made for example of the products Cyclochem 326A from Evonik Goldschmidt, Cerabeil Bio from Baerlocher, WHITE BEESWAX BP (CERA ALBA) BP/PH EUR from Tropical Forest, Beeswax 8108 from Kahl, WHITE BEESWAX SP 453P from Strahl & Pitch.

With regards to synthetic beeswaxes, mention can be made for example of the products Kester Wax K80H, Kester Wax K82P from Koster Keunen, the Syncrowax BB4 product from Croda.

The (poly)oxyalkylenated or (poly)glycerolated hydrocarbon-based waxes are more particularly natural or synthetic waxes that are in particular esterified with the corresponding polyol.

More particularly, the number of oxyalkylenated patterns can vary from 1 to 100, more particularly from 1 to 50, preferably from 1 to 20; the number of glycerolated patterns can vary from 1 to 20.

Particular mention can be made of PEG-8 Beeswax with for example the APIFIL CG product from Gattefosse or PEG-8 Beeswax from Koster Keunen), PEG-6 Beeswax; polyoxyethylene carnauba waxes such as PEG-12 Carnauba from Koster Keunen; lanolin waxes, hydrogenated or not, polyoxyethylenated, such as PEG-10 lanolin or PEG-20 lanolin.

Polyoxyethylene lanolin waxes and derivatives, in particular PPG-5 lanolin wax or PPG-5 lanolin wax glyceride are also suitable.

Montanate waxes can also be used, such as glycol montanate glycol/butylene glycol montanate waxes, such as the LICOWAX waxes sold by Clariant.

Mention can also be made of glycerolated or polyglycerolated waxes: polyglycerolated beeswax, in particular polyglyceryl-3 Beeswax (Cera Bellina Wax from Koster Keunen) and the Acacia Decurrens/Jojoba/Sunflower Seed Wax/Polyglyceryl-3 Esters mixture (Hydracire S from Gattefosse), polyglycerolated plant waxes such as mimosa, jojoba, sunflower waxes and mixtures thereof (Acacia Decurrens/Jojoba/Sunflower Seed Wax Polyglyceryl-3 Esters.

Mention can also be made of waxes corresponding to partial or total esters, preferably total, of a $C_{16}$-$C_{30}$ carboxylic, saturated, possibly hydroxylated, with glycerol. The term total esters means that all of the hydroxyl functions of the glycerol are esterified.

As an example, mention can be made of trihydroxystearine (or glyceryl trihydroxystearate), tristearine (or glyceryl tristearate), tribehenin (or glyceryl tribehenate), alone or in a mixture. Among the suitable compounds, mention can be made of glycerol triesters and of 12-hydroxystearic acid or hydrogenated castor oil, such as for example Thixcin R, Thixcin E, sold by Elementis Specialties.

As for alcohol wax, mention can be made of alcohols, preferably linear, preferably saturated, comprising from 16 to 60 carbon atoms, of which the melting point is between 25° C. and 120° C. With respect to alcohol wax, mention can be made for example of Performacol 550-L Alcohol from New Phase Technologie, stearyl alcohol, cetyl alcohol, myristyl alcohol, palm alcohol, behenic alcohol, erucic alcohol, arachidylic alcohol, or mixtures thereof.

According to a particular embodiment, the polar hydrocarbon-based wax is chosen from beeswax, synthetic beeswax, (poly)glycerolated beeswax, polyoxyethylenated beeswax, as well as mixtures thereof.

According to a preferred embodiment, the compositions of the invention comprise beeswax, polyglycerolated or polyoxyethylenated beeswax, and mixtures thereof, and preferably beeswax, polyglycerolated beeswax, as well as mixtures thereof.

Preferably, the polar hydrocarbon-based wax content ranges from 0.5% to 15% by weight, particularly from 2% to 10% by weight, and more preferably from 3% to 9% by weight, with respect to the total weight of the composition.

Additional Waxes

The compositions according to the invention can further comprise one or several additional waxes, in particular hydrocarbon-based, polar or non-polar other than the polar hydrocarbon-based waxes such as defined hereinabove, and silicone waxes.

If the composition comprises at least one additional wax, then the content in this type of wax(es) is such that the polar hydrocarbon-based wax(es)/additional wax(es) weight ratio is greater than 1, preferably greater than 1.2.

If the composition comprises at least one additional wax, then the content in additional wax(es) is less than or equal to 5% by weight (i.e. between 0 and 5% by weight), preferentially between 0.1% and 5% by weight, by weight with respect to the total weight of said composition.

Non-Polar Hydrocarbon-Based Waxes

The term "non-polar hydrocarbon-based waxes" in terms of this invention means waxes consisting only of carbon and hydrogen atoms and devoid of heteroatoms such as N or O. They are also devoid of silicon and fluorine atoms.

For the purposes of illustration of non-polar waxes suitable for the invention, mention can in particular be made of hydrocarbon-based waxes such as microcrystalline waxes, paraffin waxes, ozokerite, polymethylene waxes, polyethylene waxes, microwaxes in particular polyethylene, Fischer-Tropsch waxes.

As a polyethylene wax, mention can be made of PERFORMALENE 500-L POLYETHYLENE and PERFORMALENE 400 POLYETHYLENE sold by New Phase Technologies and ASENSA SC 211 sold by HONEYWELL.

As a polymethylene wax, mention can be made of CIREBELLE108 sold by Cirebelle.

As ozokerite mention can be made of OZOKERITE WAX SP 1020 P.

As microcrystalline waxes that can be used, mention can be made of MULTIWAX W 445® sold by SONNEBORN and MICROWAX HW® and BASE WAX 30540® sold by PARAMELT.

As microwaxes, mention can be made in particular of polyethylene microwaxes such as those sold under the names Micropoly 200®, 220®, 220L® and 250S® by MICRO POWDERS.

Polar Hydrocarbon-Based Waxes

The term "polar hydrocarbon-based waxes" means, in terms of this invention, waxes of which the chemical structure is formed primarily, or even constituted, of carbon and hydrogen atoms, and comprising at least one heteroatom such as an atom of oxygen or nitrogen.

These waves can also include one or several silicon atoms, in which case these are polar silicone waxes.

These waves can also include one or several fluorine atoms, in which case these are polar fluorine waxes.

Polar waxes devoid of this heteroatom are called polar hydrocarbon-based waxes. They may contain alcohol, ester, ether, carboxylic acid, amine and/or amide groups.

Preferably, if the composition comprises at least one additional wax, the latter is chosen from hydrocarbon-based waxes.

As a hydrocarbon-based polar wax, particularly suitable are the waxes chosen from ester waxes and alcohol waxes.

The term "ester wax" refers according to the invention to a wax that comprises at least one ester function. The ester waxes can furthermore be hydroxylated.

The term "alcohol wax" refers according to the invention to a wax that comprises at least one alcohol function, i.e. that comprises at least one free hydroxyl (OH) group.

The following can in particular be used as an ester wax i) the waxes having formula $R_1COOR_2$ wherein $R_1$ and $R_2$ are aliphatic linear, branched or cyclic chains of which the number of atoms varies from 10 to 50, that can contain a heteroatom such as O, N or P and of which the melting point temperature varies from 25° C. to 120° C. In particular, it is possible to use as ester wax a $C_{20}$-$C_{40}$ (hydroxystearyloxy) alkyl stearate (with the alkyl group comprising from 20 to 40 carbon atoms), alone or in a mixture or a $C_{20}$-$C_{40}$ alkyl stearate. Such waxes are particular sold under the names "Kester Wax K 82 P®", "Hydroxypolyester K 82 P®", "Kester Wax K 80 P®", or "KESTER WAX K82H" by KOSTER KEUNEN.

ii) di-(trimethylol-1,1,1 propane) tetrastearate, sold under the name Hest 2T-4S® by HETERENE.

iii) diester waxes of a carboxylic diacid having general formula $R_3$—(—OCO—$R_4$—COO—$R_5$), wherein $R_3$ and $R_5$ are identical or different, preferably identical and is a $C_4$-$C_{30}$ alkyl group (alkyl group comprising from 4 to 30 carbon atoms) and $R_4$ is a $C_4$-$C_{30}$ linear or branched aliphatic group (alkyl group comprising from 4 to 30 carbon atoms) and which can contain or not one or several unsaturations. Preferably, the $C_4$-$C_{30}$ aliphatic group is linear and unsaturated.

iv) Mention can also be made of the waxes obtained by catalytic hydrogenation of animal or plant oils that have $C_8$-$C_{32}$ linear or branched fat chains, for example such as hydrogenated jojoba oil, hydrogenated sunflower oil, hydrogenated castor oil, hydrogenated coconut oil, as well as the waxes obtained by hydrogenating esterified castor oil with cetyl alcohol, such as those sold under the names Phytowax ricin 16L64® and 22L73® by SOPHIM. Such waxes are described in application FR-A-2792190. As waxes obtained by hydrogenating esterified olive oil with stearyl alcohol, mention can be made of those sold under the name "PHYTOWAX Olive 18 L 57".

v) Mention can also be made of carnauba wax, candellila wax, rice bran wax, Ouricury wax, Alfa wax, cork fiber wax, sugarcane wax, Japan wax, sumac wax, montan wax, Orange wax, Bay leaf wax, hydrogenated Jojoba wax, and mixtures thereof.

Silicone Waxes

The composition can also comprise at least one silicone wax in particular obtained by esterification with a (poly) alkoxylated silicone such as silicone beeswax, silicone candelilla wax, silicone carnauba wax, and mixtures thereof.

Preferably, the additional wax or waxes are chosen from non-polar hydrocarbon-based waxes.

According to an advantageous embodiment of the invention, the composition comprises at least one additional wax, chosen from non-polar waxes.

Non-Ionic Silicone or Hydrocarbon-Based Surfactants

The compositions of the invention comprise at least one hydrocarbon-based or silicone non-ionic surfactant.

The surfactant or surfactants are chosen such that the composition according to the invention is in the form of a water-in-oil emulsion.

Preferably, the surfactant has an HLB (hydrophilic/lipophilic balance) less than or equal to 8, more particularly less than or equal to 7, preferably between 1 and 6. The HLB value according to GRIFFIN is defined in J. Soc. Cosm. Chem. 1954 (volume 5), pages 249-256.

Silicone Surfactants

With regards to silicone surfactants, mention can be made of alkyl or alkoxy dimethicone copolyols with pendant alkyl or alkoxy chain or silicone backbone-end having for example from 6 to 22 carbon atoms; dimethicone copolyols, which are more particularly oxypropylene and/or oxyethylene polydimethyl methyl siloxanes, as well as cross-linked solid elastomeric organopolysiloxanes that comprise at least one oxyalkylene group, and mixtures thereof.

As an example of alkyl or alkoxy dimethicone copolyols, mention can be made of compounds having the following formula (I):

$$(CH_3)_3Si-O-\left[\begin{array}{c}CH_3\\|\\Si-O\\|\\(CH_2)_p\\|\\CH_3\end{array}\right]_o\left[\begin{array}{c}CH_3\\|\\Si-O\\|\\(CH_2)_q\\|\\O\\|\\PE\end{array}\right]_m\left[\begin{array}{c}CH_3\\|\\Si-O\\|\\CH_3\end{array}\right]_n-Si(CH_3)_3 \quad (I)$$

in which:

PE is (—$C_2H_4O$)$_x$—($C_3H_6O$)$_y$—R, R being chosen from a hydrogen atom and an alkyl radical from 1 to 4 carbon atoms, x ranging from 0 to 100 and y ranging from 0 to 80, x and y not being simultaneously 0; preferably R is a hydrogen atom;

m varies from 1 to 40; preferably from 1 to 10;

n varies from 10 to 200; preferably from 10 to 100;

o varies from 1 to 100; preferably from 1 to 30;

p varies from 5 to 21, more particularly from 7 to 21;

q varies from 0 to 4, from 1 to 3.

As examples of dimethicone copolyols, those corresponding more particularly to the following formula (II) can be used:

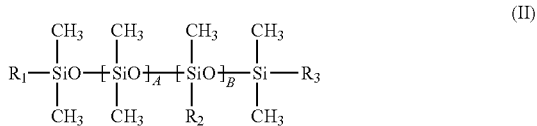

in which:

$R_1$, $R_2$, $R_3$, independently of each other, are a $C_1$-$C_6$ alkyl radical or a —($CH_2$)$_x$—(O$CH_2CH_2$)$_y$—(O$CH_2CH_2$)$_z$—O$R_4$ radical, at least one radical $R_1$, $R_2$ or $R_3$ being not an alkyl radical; $R_4$ being a hydrogen, a $C_1$-$C_3$ alkyl radical or a $C_2$-$C_4$ acyl radical;

A is an integer varying from 0 to 200;

B is an integer varying from 0 to 50; provided that A and B are not equal to zero at the same time;

x is an integer varying from 1 to 6;

y is an integer varying from 1 to 30; and z is an integer varying from 0 to 30, preferably from 0 to 20.

Among the particularly preferred silicone surfactants, mention can be made of:

dimethicone copolyols such as for example those sold under the names KF-6015 (PEG-3 dimethicone), KF-6016 (PEG-9 methyl ether dimethicone), KF-6017 (PEG-10 dimethicone), KF-6028 (PEG-9 polydimethylsiloxyethyl dimethicone), KF-6050 L (PEG/PPG 18/18 dimethicone in cyclopentasiloxane), X-22-6711D (dimethicone PEG/PPG-18/18 Dimethicone) by Shin-Etsu; the dimethicone copolyols sold under the names Dow Corning 3225C® (PEG/PPG-18/18 DIMETHICONE in a mixture of cyclotetrasiloxane and cyclopentasiloxane), DC 5225 C Formulation Aid (PEG/PPG-18/18 dimethicone in cyclopentasiloxane); or the product sold under the name SF 1528 GE (mixture of PEG/PPG-20/15 Dimethicone and cyclopentasiloxane) by Momentive Performance Materials.

Alkyl-dimethicone copolyols can also be used such as Lauryl PEG/PPG-18/18 Methicone (which is more particularly an alkoxyl derivative of Lauryl Methicone containing on the average 18 moles of ethylene oxide and 18 moles of propylene oxide, sold under the name "Dow Corning 5200 Formulation Aid" by Dow Corning; cetyl PEG/PPG-10/1 Dimethicone (which is more particularly a copolymer of Cetyl Dimethicone and an alkoxyl derivative of dimethicone containing on the average 10 moles of ethylene oxide and 1 mole of propylene oxide) such as the product sold under the name Abil EM 90 by Evonik Goldschmidt as well as the mixture of cetyl PEG/PPG-10/1 Dimethicone, of polyglycerol isostearate (4 moles) and hexyl laurate sold under the name ABIL WE 09 by Evonik Goldschmidt.

It is also possible to mention, as emulsion surfactants, in particular for water-in-oil emulsions, cross-linked solid elastomeric organopolysiloxanes comprising at least one oxyalkylene group, such as those obtained according to the operating procedure in examples 3, 4 and 8 of document U.S. Pat. No. 5,412,004 and the examples of document U.S. Pat. No. 5,811,487, particularly the product of example 3 (example of synthesis) of the U.S. Pat. No. 5,412,004 and such as the products sold under the references KSG 21, KSG-210, by Shin Etsu.

Preferably, as a C8-C22 dimethicone copolyol alkyl, cetyl dimethicone copolyol is used, in particular of which the INCI name is CETYL PEG/PPG-10/1 DIMETHICONE, such as the product sold under the name Abil EM-90 by Evonik Goldschmidt.

Hydrocarbon-Based Surfactants

Non-ionic surfactants can be chosen in particular from alkyl($C_8$-$C_{30}$) ethers of poly(ethylene oxide), alkyl($C_8$-$C_{30}$)—and polyalkyl($C_8$-$C_{30}$)—esters of ethylene oxide, of propylene, of poly(ethylene oxide) or of poly(propylene oxide); fatty acid polyesters, preferably polyhydroxylated, $C_{12}$-$C_{20}$, polyoxyalkylenated, having from 4 to 50 moles of ethylene oxide; alkyl- and polyalkyl- esters of sorbitan; alkyl- and polyalkyl- esters of (poly)glycerol and mixtures thereof.

As alkyl($C_8$-$C_{30}$)—ethers of poly(ethylene oxide), preference is given to the use of those that have a number of ethylene oxide (EO) residues ranging from 2 to 4. As examples, particular mention can be made of laureth-2; steareth-2, oleth-2; oleth-3; ceteth-2; ceteareth-3.

As alkyl($C_8$-$C_{30}$)—and polyalkyl($C_8$-$C_{30}$)—esters of ethylene oxide, of propylene, of poly(ethylene oxide) or of poly(propylene oxide), preference is given to the use of those that have a number of ethylene oxide (EO) residues ranging from 1 to 5, with for example glycol distearate, glycol stearate, PEG-2 oleate; EPG-3 oleate; PEG-4 dilaurate, propylene glycol isostearate; PEG-2.5 castor oil; PEG-3 castor oil.

As other surfactants that can be used, mention can be made of $C_{12}$-$C_{20}$ fatty acid polyesters, preferably polyhydroxylated, polyoxyalkylenated, having from 4 to 50 moles of ethylene oxide, that have water-in-oil emulsifying properties.

In particular, these polymers are sequenced polymers, preferably with an ABA structure, comprising poly(hydroxyl ester) sequences and polyethyleneglycol sequences.

The fatty acid of said emulsifying polymer such as defined hereinabove has preferably from 14 to 18 carbon atoms.

The esters can in particular be chosen from olates, palmitates or stearates. The polyethyleneglycol sequences of said emulsifying polymer such as defined hereinabove preferably have from 20 to 40 moles of ethylene oxide.

A polymer surfactant that is particularly suitable for the realization of the compositions of the invention is di-polyhydroxystearate of polyethylene glycol with 30 EO sold under the trade name Arlacel P 135 by Croda.

As alkyl($C_8$-$C_{30}$)—and polyalkyl($C_8$-$C_{30}$)—esters of sorbitan, particular mention can be made of sorbitan trioleate, sorbitan sesquioleate, sorbitan oleate, sorbitan palmitate; sorbitan stearate, sorbitan isostearate, mixtures of sorbitan stearate and of sucrose cocoate or sorbitan and glycerol isostearate (Arlacel 986 sold by Croda), and mixtures thereof.

As alkyl($C_8$-$C_{30}$)—and polyalkyl($C_8$-$C_{30}$)—esters of (poly)glycerol, preference is given to the use of those that have a number of glycerol residues ranging from 1 to 4.

Mention can be made for example of polyglyceryl-4 isostearate (Isolan GI 34 sold by Evonik Goldschmidt); polyglyceryl-3 diisostearate (LAMEFORM TGI sold by Cognis), glyceryl stearate, glyceryl laurate, alone or in mixtures.

According to a particularly preferred embodiment, the composition comprises at least one non-ionic silicone surfactant.

Advantageously, the silicone surfactant or surfactants are chosen from dimethicone copolyols, alkyl dimethicone copolyols described hereinabove, in particular alkyl $C_8$-$C_{22}$ dimethicone copolyols in particular having formula (I), alone or in mixtures.

According to a particular embodiment of the invention, the composition also comprises at least one non-ionic hydrocarbon-based (co-surfactant) surfactant, very particularly alkyl- and polyalkyl- esters of (poly)glycerol and/or of sorbitan, and preferably polyglyceryl-3 diisostearate, polyglyceryl-4 isostearate, sorbitan isostearate or sorbitan and glycerol isostearate.

The content in non-ionic silicone or hydrocarbon-based surfactant(s) represents more particularly a content ranging from 2 to 10% by weight, and preferably ranging from 3 to 8% by weight with respect to the total weight of the cosmetic composition.

Additional Surfactants

The composition according to the invention can optionally comprise one or several additional surfactants chosen from non-ionic hydrocarbon-based surfactants with an HLB value greater than 8, hydrocarbon-based or silicone, and preferably hydrocarbon-based; among the ionic in particular anionic hydrocarbon-based surfactants.

If they are present, their content is such that the composition is in the form of a water-in-oil emulsion.

Non-Volatile Silicone Oils

In addition to non-volatile H1 and H2 oils such as defined hereinabove, the compositions of the invention can further comprise at least one non-volatile silicone oil.

Among the non-volatile silicone oils that can be used in this invention, mention can be made for example of non-phenylated non-volatile silicone oils and phenylated non-volatile silicone oils.

The silicone oils that can be used within of the invention advantageously have a molecular weight less than or equal to 150,000 g/mol, preferably less than or equal to 100,000 g/mol, and better less than or equal to 10,000 g/mol.

The term "silicone oil" refers to an oil containing at least one silicon atom and particularly containing Si-O groups.

Non-Phenylated Non-Volatile Silicone Oils

The expression "non-phenylated silicone oil" designates a silicone oil that does not comprise any phenyl substituents.

Examples that are representative of these non-phenylated non-volatile silicone oils that can be mentioned, comprise polydimethylsiloxanes; alkyldimethicones; vinylmethylmethicones.

Note that these non-phenylated non-volatile silicone oils do not contain any residue(s) of the ethylene oxide, propylene oxide or glycerol type. They are therefore different from the silicone surfactants described hereinabove.

Moreover, the term "dimethicone" (INCI name) corresponds to a polydimethylsiloxane (chemical name).

In particular, these oils can be chosen from the following non-volatile oils:

polydimethylsiloxanes (PDMS),
alkyldimethicones comprising aliphatic groups, in particular alkyl, or alkoxy, which are pendant and/or at the end of the silicone chain; these groups each comprise from 2 to 24 carbon atoms. As an example mention can be made of cetyldimethicone sold under the trade name ABIL WAX 9801 from Evonik Goldschmidt,
polydimethylsiloxanes comprising functional groups such as hydroxyl groups,
substituted polydimethylsiloxane aliphatic groups, in particular $C_2$-$C_{24}$ alkyl, pendant and/or at the end of the silicone chain, and by functional groups such as hydroxyl groups,
mixtures thereof.

Preferably, these non-phenylated non-volatile silicone oils are chosen from polydimethylsiloxanes; alkyldimethicones and also from polydimethylsiloxanes substituted with aliphatic groups, in particular $C_2$-$C_{24}$ alkyl, and functional groups such as hydroxyl groups.

The non-phenylated non-volatile silicone oil may particularly be chosen from silicones having formula (I):

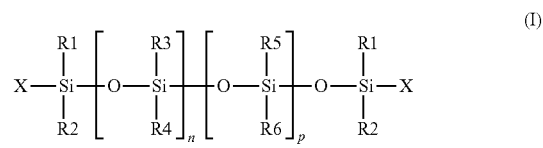

wherein:
$R_1$, $R_2$, $R_5$ and $R_6$ are, together or separately, an alkyl radical containing 1 to 6 carbon atoms,
$R_3$ and $R_4$ are, together or separately, an alkyl radical containing 1 to 6 carbon atoms or a hydroxyl radical,
X is an alkyl radical containing 1 to 6 carbon atoms or a hydroxyl radical,
n and p are integers chosen in such a way as to have a fluid compound, in particular of which the viscosity at 25° C. is between 8 centistokes (cSt) ($8 \times 10^{-6}$ m$^2$/s) and 800,000 cSt, advantageously less than 100,000 cSt, and advantageously a mean molar mass by weight less than or equal to 150,000 g/mol, preferably less than or equal to 100,000 g/mol, and better less than or equal to 10,000 g/mol.

As non-volatile non-phenylated silicone oils suitable for the realization of the invention, mention can be made of those for which:
the substituents $R_1$ to $R_6$ and X represent a methyl group, and p and n are such that the viscosity is 60,000 cSt, for example the product sold under the name Dow Corning 200 Fluid 60000 CS by Dow Corning, and the product sold under the name Wacker Belsil DM 60000 by Wacker,
the substituents $R_1$ to $R_6$ and X represent a methyl group, and p and n are such that the viscosity is 100 cSt, or 350 cSt, for example the products sold respectively under the names Belsil DM100, Dow Corning 200 Fluid 350 CS, by Dow Corning, and
the substituents $R_1$ to $R_6$ represent a methyl group, the group X represents a hydroxyl group, and n and p are such that the viscosity is 700 cSt, for example the product sold under the name Baysilone Fluid T0.7 by Momentive.

Non-Volatile Phenylated Silicone Oils

The expression "phenylated silicone oil" designates a silicone oil that has at least one phenyl substituent.

These non-volatile phenylated silicone oils can be chosen from those that furthermore have at least one dimethicone fragment, or from those that do not have any. Note that the terms "dimethicone fragment" designate a divalent siloxane group of which the silicon atom carried two methyl radicals, with this group not being located at the ends of the molecule. It can be represented by the following formula:

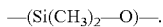

The non-volatile phenylated silicone oil can as such be chosen from:

phenylated silicone oils that have or do not have a dimethicone fragment corresponding to the following formula (I):

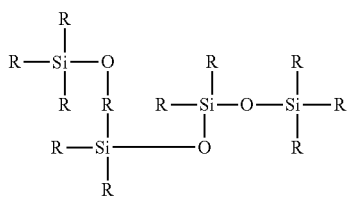

wherein the R groups, monovalent or divalent, are, independently from one another, a methyl, methylene, phenyl or phenylene, provided that at least one R group is a phenyl.

Preferably, in this formula, the phenylated silicone oil comprises at least three phenyl groups, for example at least four, at least five or at least six.

phenylated silicone oils that have or do not have a dimethicone fragment corresponding to the following formula (2):

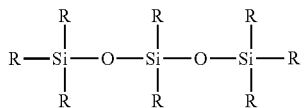

wherein the R groups are, independently from one another, a methyl or a phenyl, provided that at least one R group is a phenyl.

Preferably, in this formula, the compound of formula (II) comprises at least three phenyl groups, for example at least four or at least five.

formula (II) in which at least 4 or at least 5 radicals R are a phenyl radical with the remaining radicals being methyls.

Such non-volatile phenylated silicone oils are preferably trimethylpentaphenyl-trisiloxane, or tetramethyl-tetraphenyl-trisiloxane. They are in particular sold by Dow Corning under the reference PH-1555 HRI or Dow Corning 555 Cosmetic Fluid (chemical name: 1,3,5-trimethyl-1,1,3,5,5-pentaphenyl-trisiloxane; INCI name: trimethyl-pentaphenyltrisiloxane), or tetramethyl-tetraphenyl-trisiloxane sold under the reference Dow Corning 554 Cosmetic Fluid by Dow Corning can also be used.

They correspond in particular to the following formulas (III) and (III'):

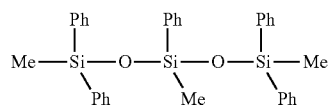

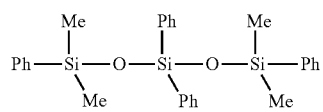

wherein Me represents methyl, Ph represents phenyl.

phenylated silicone oils that at least one dimethicone fragment corresponding to the following formula (IV):

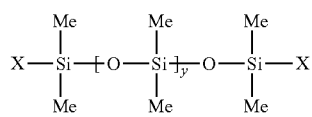

wherein Me represents methyl, y is between 1 and 1,000 and X represents —$CH_2$—$CH(CH_3)$(Ph).

phenylated silicone oils corresponding to the formula (V) hereinbelow, and mixtures of the latter:

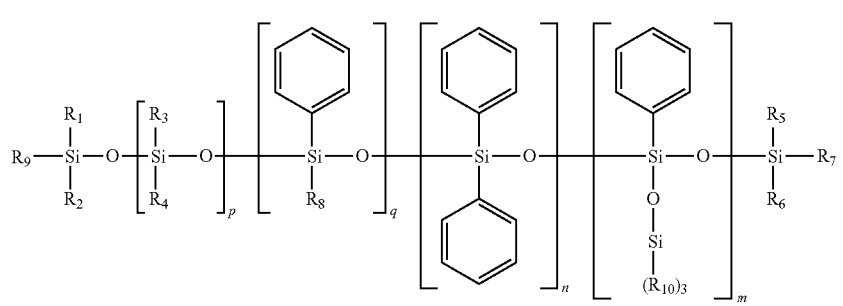

Mixtures of the various phenylorganopolysiloxane compounds described hereinabove may be used.

Examples that can be mentioned comprise mixtures of triphenyl-, tetraphenyl- or pentaphenyl-organopolysiloxanes.

Among the compounds having formula (II), more particular mention can be made of phenylated silicone oils that do not have any dimethicone fragment corresponding to the wherein:

$R_1$ to $R_{10}$, independently of each other, are $C_1$-$C_{30}$ linear, cyclic or branched, saturated or unsaturated hydrocarbon radicals, m, n, p and q are, independently of each other, integers between 0 and 900, provided that the sum m+n+q is different to 0.

Preferably, the sum m+n+q is between 1 and 100. Advantageously, the sum m+n+p+q is between 1 and 900 and preferably between 1 and 800.

Preferably, q is equal to 0.

More particularly, $R_1$ to $R_{10}$, independently of one other, are a linear or branched, saturated or unsaturated, preferably saturated, $C_1$-$C_{30}$ hydrocarbon radical, and in particular a $C_1$-$C_{20}$ hydrocarbon radical, preferably saturated, in particular $C_1$-$C_{18}$, or a $C_6$-$C_{14}$ aryl radical and in particular $C_{10}$-$C_{13}$, monocyclic or polycyclic, or an aralkyl radical preferably of which the alkyl portion is $C_1$-$C_3$.

Preferably, $R_1$ to $R_{10}$ may each represent a methyl, ethyl, propyl, butyl, isopropyl, decyl, dodecyl or octadecyl radical, or alternatively a phenyl, tolyl, benzyl or phenethyl radical. $R_1$ to $R_{10}$ may in particular be identical and, moreover, may be a methyl radical.

As particular embodiments of the formula (V), mention can be made of:

phenylated silicone oils that have or do not have at least one dimethicone fragment corresponding to the formula (VI) hereinbelow, and mixtures of the latter:

$$\text{(VI)}$$

$$H_3C-\underset{R_2}{\underset{|}{\overset{R_1}{\overset{|}{Si}}}}-O-\left[\underset{R_4}{\underset{|}{\overset{R_3}{\overset{|}{Si}}}}-O\right]_p-\left[\underset{\underset{Ph}{|}}{\overset{\overset{Ph}{|}}{Si}}-O\right]-\left[\underset{\underset{Si(CH_3)_3}{|}}{\overset{\overset{O}{|}}{Si}}-O\right]_m-\underset{R_6}{\underset{|}{\overset{R_5}{\overset{|}{Si}}}}-CH_3$$

wherein:
$R_1$ to $R_6$, independently of one other, are $C_1$-$C_{30}$ saturated or unsaturated, linear, cyclic or branched hydrocarbon radicals, an aryl radical, preferably $C_6$-$C_{14}$, or an aralkyl radical of which the alkyl portion is $C_1$-$C_3$.

m, n and p are, independently of one other, integers between 0 and 1,000, and preferably between 0 and 100, provided that the sum n+m is between 1 and 1,000, and preferably between 1 and 100.

Preferably, $R_1$ to $R_6$, independently of one other, are a $C_1$-$C_{20}$ hydrocarbon radical, preferably alkyl, in particular $C_1$-$C_{18}$, or a $C_6$-$C_{14}$ monocyclic aryl radical (preferably $C_6$) or polycyclic and in particular $C_{10}$-$C_{13}$, or an aralkyl radical (preferably the aryl portion is $C_6$; the alkyl portion is $C_1$-$C_3$).

Preferably, $R_1$ to $R_6$ may each represent a methyl, ethyl, propyl, butyl, isopropyl, decyl, dodecyl or octadecyl radical, or alternatively a phenyl, tolyl, benzyl or phenethyl radical.

$R_1$ to $R_6$ may in particular be identical and, moreover, may be a methyl radical. Preferably, m=1 or 2 or 3, and/or n=0 and/or p=0 or 1 can be applied, in formula (VI).

According to a particular embodiment, the non-volatile phenylated silicone oil is chosen from the phenylated silicone oils that have at least one dimethicone fragment.

Preferably, such oils correspond to compounds having the formula (VI) wherein:
m=0 and n and p are, independently of each other, integers between 1 and 100.
Preferably, $R_1$ to $R_6$ are methyl radicals.

According to this embodiment, the silicone oil is preferably chosen from a diphenyldimethicone such as KF-54 from Shin Etsu (400 cSt), KF54HV from Shin Etsu (5000 cSt), KF-50-300CS from Shin Etsu (300 cSt), KF-53 from Shin Etsu (175 cSt), KF-50-100CS from Shin Etsu (100 cSt).

p is between 1 and 1,000, the sum n+m is between 1 and 1,000, and n=0.

These phenylated silicone oils that have or do not have at least one dimethicone fragment correspond more particularly to the formula (VII) hereinbelow:

$$\text{(VII)}$$

$$Me-\underset{Me}{\underset{|}{\overset{Me}{\overset{|}{Si}}}}-\left[O-\underset{Me}{\underset{|}{\overset{Me}{\overset{|}{Si}}}}\right]_p-\left[O-\underset{Ph}{\underset{|}{\overset{OR'}{\overset{|}{Si}}}}\right]_m-O-\underset{Me}{\underset{|}{\overset{Me}{\overset{|}{Si}}}}-Me$$

wherein Me is methyl and Ph is phenyl, OR' is a —OSiMe$_3$ group and p is 0 or is between 1 and 1000, and m is between 1 and 1000. In particular, m and p are such that the compound (VII) is a non-volatile oil.

According to a first embodiment of non-volatile phenylated silicone that has at least one dimethicone fragment, p is between 1 and 1000. m is more particularly such that the compound (VII) is a non-volatile oil. For example, trimethylsiloxyphenyldimethicone can be used, sold in particular under the reference Belsil PDM 1000 by Wacker.

According to a second embodiment of non-volatile phenylated silicone that do not have any dimethicone fragment, p is equal to 0. m is between 1 and 1000, and in particular, is such that the compound (VII) is a non-volatile oil.

For example, phenyltrimethicone can be used, sold in particular under the reference Dow Corning 556 Cosmetic Grade Fluid (DC556).

non-volatile phenylated silicone oils that do not have any dimethicone fragment corresponding to the formula (VIII) hereinbelow, and mixtures of the latter:

$$\text{(VIII)}$$

$$H_3C-\underset{R}{\underset{|}{\overset{R}{\overset{|}{Si}}}}-O-\left[\underset{\underset{Ph}{|}}{\overset{\overset{Ph}{|}}{Si}}-O\right]_n-\left[\underset{\underset{Si(CH_3)_3}{|}}{\overset{\overset{O}{|}}{Si}}-O\right]_m-\underset{R}{\underset{|}{\overset{R}{\overset{|}{Si}}}}-CH_3$$

wherein:
R, independently of each other, are $C_1$-$C_{30}$, saturated or unsaturated, linear, cyclic or branched, hydrocarbon radicals, preferably R is a $C_1$-$C_{30}$ alkyl radical, an aryl radical, preferably in $C_6$-$C_{14}$, or an aralkyl radical of which the alkyl portion is $C_1$-$C_3$.

m and n are, independently of one other, integers between 0 and 100, provided that the sum n+m is between 1 and 100.

More preferably, R, independently of each other, are a $C_1$-$C_{30}$, saturated or unsaturated, linear or branched, preferably saturated, hydrocarbon radical, and in particular a $C_1$-$C_{20}$ hydrocarbon radical, preferably saturated, in particular in $C_1$-$C_{18}$ and more particularly in $C_4$-$C_{10}$, a $C_6$-$C_{14}$ monocyclic or polycyclic aryl radical and in particular in $C_{10}$-$C_{13}$, or an aralkyl radical preferably the aryl portion is $C_6$ and the alkyl portion is $C_1$-$C_3$.

Preferably, the radicals R may each represent a methyl, ethyl, propyl, butyl, isopropyl, decyl, dodecyl or octadecyl radical, or alternatively a phenyl, tolyl, benzyl or phenethyl radical.

The radicals R may in particular be identical and, moreover, may be a methyl radical.

Preferably, m=1 or 2 or 3, and/or n=0 and/or p=0 or 1 can be applied, in formula (VIII).

According to a preferred embodiment, n is an integer between 0 and 100 and m is an integer between 1 and 100, provided that the sum n+m is between 1 and 100, in the formula (VIII). Preferably, R is a methyl radical.

According to one embodiment, a phenylated silicone oil having formula (VIII) having a viscosity at 25° C. between 5 and 1500 mm²/s (i.e., from 5 to 1500 cSt), and preferably having a viscosity between 5 and 1000 mm²/s (i.e. 5 to 1000 cSt) can be used.

According to this embodiment, the non-volatile phenylated silicone oil is preferably chosen from phenyltrimethicones (when n=0) such as DC556 from Dow Corning (22.5 cSt), or from diphenylsiloxyphenyltrimethicone oil (when m and n are between 1 and 100) such as KF56 A from Shin Etsu, Silbione oil 70663V30 from Rhône-Poulenc (28 cSt). The values between brackets represent the viscosities at 25° C.

phenylated silicone oils that have or do not have at least one dimethicone fragment corresponding to the following formula, and mixtures of the latter:

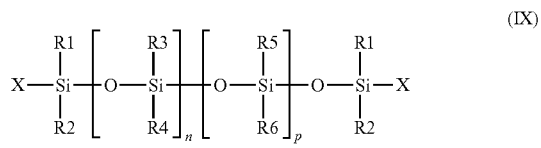

(IX)

wherein:

$R_1$, $R_2$, $R_5$ and $R_6$ are, identical or not, an alkyl radical containing 1 to 6 carbon atoms, $R_3$ and $R_4$ are, identical or not, an alkyl radical containing 1 to 6 carbon atoms or an aryl radical (preferably $C_6$-$C_{14}$), with the condition that at least one of $R_3$ and $R_4$ is a phenyl radical, X is an alkyl radical containing 1 to 6 carbon atoms, a hydroxyl radical or a vinyl radical, n and p being an integer greater than or equal to 1, chosen in such a way as to confer to the oil a mean molar mass by weight preferably less than 150,000 g/mole and more preferably less than 100,000 g/mole.

and a mixture of the latter.

More particularly, the composition comprises at least one non-volatile silicone oil chosen from polydimethylsiloxanes; non-volatile phenylated silicone oils that do not have any dimethicone fragment, as well as mixtures thereof, and preferably non-volatile phenylated silicone oils that do not have any dimethicone fragment.

Very advantageously, the composition comprises at least one non-volatile silicone oil chosen from phenyl trimethicone, trimethylpentaphenyl-trisiloxane, tetramethyl-tetraphenyl-trisiloxane, and mixtures thereof, preferably phenyltrimethicone.

If the composition contains any, the non-volatile silicone oil(s) content represents from 2% to 10% by weight, preferentially from 3% to 8% by weight, with respect to the weight of the composition.

Volatile Oils

The composition according to the invention can optionally comprise at least one volatile oil, chosen more particularly from volatile hydrocarbon-based or silicone oils.

The term volatile oil refers to an oil that has a non-zero vapor pressure, at ambient temperature (25° C.) and atmospheric pressure, ranging in particular from 0.13 Pa to 40,000 Pa, in particular ranging to 13,000 Pa, and more particularly ranging to 1,300 Pa.

The volatile hydrocarbon-based oils are preferably chosen from non-polar hydrocarbon-based oils and in particular can be chosen from volatile hydrocarbon-based oils that have from 8 to 16 carbon atoms and mixtures thereof, and in particular:

$C_8$-$C_{16}$ branched alkanes such as iso-alkanes (also called isoparaffins) in $C_8$-$C_{16}$, isododecane, isodecane, isohexadecane, and for example the oils sold under the trade names Isopars or Permetyls, linear alkanes, for, example such as n-dodecane (C12) and n-tetradecane (C14) sold by Sasol respectively under the references PARAFOL 12-97 and PARAFOL 14-97, as well as mixtures thereof, the undecane-tridecane mixture (Cetiol UT), the mixtures of n-undecane (C11) and of n-tridecane (C13) obtained in examples 1 and 2 of application WO2008/155059 of Cognis, and mixtures thereof.

The volatile silicone oil may be chosen from linear, branched or cyclic silicone oils such as polydimethylsiloxanes (PDMS) having 3 to 7 silicon atoms.

By way of example of such oils, mention may be made of octyltrimethicone, hexyltrimethicone, methyl trimethicone, decamethylcyclopentasiloxane, octamethylcyclotetrasiloxane dodecamethylcyclo-hexasiloxane, decamethyltetrasilaxane, polydimethysiloxanes such as those sold under the reference DC 200 (1.5 cSt), DC 200 (5 cSt), DC 200 (3 cSt) by Dow Corning, of KF 96 A of Shin Etsu; alone or in mixtures.

If the composition contains any, the content in volatile oil(s) is between 1% and 8% by weight, with respect to the weight of the composition.

Pasty Fats

The compositions according to the invention may further comprise one or a plurality of pasty fats (or pasty compounds).

According to an embodiment, the compositions of the invention further comprise at least one pasty fat, in a content ranging from 5% to 20%, preferably from 10% to 15%, by weight in relation to the total weight of said composition.

For the purposes of the invention, the term "pasty fat" refers to a lipophilic fatty compound having a reversible solid/liquid change of state, having in the solid state, an anisotropic crystalline organization, and comprising at a temperature of 23° C. a liquid fraction and a solid fraction.

In other words, the initial melting point of the pasty compound may be less than 23° C. The liquid fraction of the pasty compound measured at 23° C. may represent 9 to 97% by weight of the compound. This liquid fraction at 23° C. preferably represents between 15 and 85%, more preferably between 40 and 85% by weight.

The melting point of a solid fat can be measured using a differential scanning calorimeter (DSC), for example the calorimeter sold under the trade name "DSC Q100" by TA Instruments with the "TA Universal Analysis" software, according to the protocol defined hereinabove.

According to the invention, the melting temperature corresponds to the temperature of the most endothermic peak observed in DSC as described in the norm ISO 11357-3; 1999.

The measurement protocol is as follows:

A sample of solid fat of about 5 mg is placed in a "sealed aluminum capsule" crucible.

The sample is subjected to a first temperature rise from 20° C. to 80° C., at a heating rate of 2° C./minute to 80° C., then left at isotherm of 80° C. for 20 minutes, then is cooled from 80° C. to −80° C. at a cooling rate of 2° C./minute, and finally subjected to a second temperature rise from −80° C. to 20° C. at a heating rate of 2° C./minute.

The value of the melting temperature of the solid fat is the value of the top of the most endothermic peak of the fusion curve observed, representing the variation in the difference in power absorbed as a function of the temperature.

The liquid fraction by weight of the pasty compound at 23° C. is equal to the ratio of the enthalpy of fusion consumed at 23° C. to the enthalpy of fusion of the pasty compound.

The enthalpy of fusion of the pasty compound is the enthalpy consumed by the compound to change from the solid state to the liquid state. The pasty compound is said to be in the solid state when the entire mass thereof is in solid crystalline form. The pasty compound is said to be in the liquid state when the entire mass thereof is in liquid form.

The enthalpy of fusion of the pasty compound is equal to the area under the curve of the thermogram obtained using a differential scanning calorimeter. The enthalpy of fusion of the pasty compound is the quantity of energy required to change the compound from the solid state to the liquid state. It is expressed in J/g.

The enthalpy of fusion consumed at 23° C. is the quantity of energy required by the sample to change from the solid state to the state presented at 23° C. consisting of a liquid fraction and a solid fraction.

The pasty fat can be chosen from synthetic compounds and plant-based compounds. A pasty fat may be obtained by means of synthesis from plant-based starting materials.

The pasty compound is advantageously chosen from:
lanolin and its derivatives, such as lanolin alcohol, oxyethylenated lanolins, acetylated lanolin, lanolin esters such as isopropyl lanolate, oxypropylenated lanolins;
petroleum jelly, particularly that for which the INCI name is petrolatum and sold under the name ULTIMA WHITE PET USP by Perenco, VASELINE BLANCHE CODEX 236 from Aiglon, SNOW WHITE PET USP from Calumet Speciality;
polyol ethers chosen from pentaerythritol and polyalkylene glycol ethers, fatty alcohol and sugar ethers, and mixtures thereof, pentaerythritol and polyethylene glycol ether comprising 5 oxyethylene units (5 OE) (CTFA name: PEG-5 Pentaerythrityl Ether), pentaerythritol and polypropylene glycol ether comprising 5 oxypropylene units (5 OP) (CTFA name: PPG-5 Pentaerythrityl Ether), and the mixtures thereof and more specifically the mixture of PEG-5 Pentaerythrityl Ether, PPG-5 Pentaerythrityl Ether and soybean oil, sold under the name "Lanolide" by Vevy, wherein the ratio of the constituents by weight is 46:46:8: 46% PEG-5 Pentaerythrityl Ether, 46% PPG-5 Pentaerythrityl Ether and 8% soybean oil;
liposoluble polyethers derived from polyetherification between one or a plurality of C2-C100, preferably C2-C50, diols.

Of the liposoluble polyethers, ethylene-oxide and/or propylene-oxide copolymers with C6-C30 long-chain alkylene-oxides are particularly preferred, more preferably such that the weight ratio of ethylene-oxide and/or propylene-oxide with alkylene-oxides in the copolymer is 5:95 to 70:30. In this family, particular mention may be made of copolymers such as long-chain alkylene-oxides arranged in blocks having a mean molecular weight of 1000 to 10,000, for example a polyoxyethylene/polydodecyl glycol block copolymer such as the dodecanediol (22 mol) and polyethylene glycol (45 OE) ethers marketed under the brand ELFACOS ST9 by Akzo Nobel, esters and polyesters, and/or mixtures thereof.

Among the esters, particular preference is given to:

glycerol oligomer esters, particularly diglycerol esters, in particular adipic acid and glycerol condensates, for which part of the hydroxyl groups of the glycerols have reacted with a mixture of fatty acids such as stearic acid, capric, stearic acid and isostearic acid and 12-hydroxystearic acid, preferably such as bis-diglyceryl polyacyladipate-2 sold under the brand Softisan 649 by Sasol.

homopolymers of vinyl ester having $C_8$-$C_{30}$ alkyl groups, such as polyvinyl laurate (in particular sold under the reference Mexomère PP by Chimex), arachidyl propionate sold under the trade name Waxenol 801 by Alzo, phytosterol esters, triglycerides of fatty acids and derivatives thereof, such as for example, the partially or totally hydrogenated, particularly $C_{10}$-$C_{18}$, fatty acid triglycerides such as those sold under the reference Softisan 100 by Sasol, pentaerythritol esters non-cross-linked polyesters derived from polycondensation between a dicarboxylic acid or a $C_4$-$C_{60}$ linear or branched carboxylic acid and a diol or an $C_2$-$C_{50}$ polyol, aliphatic esters of esters derived from the esterification of an aliphatic hydroxycarboxylic acid ester with an aliphatic carboxylic acid. Preferably, the aliphatic carboxylic acid comprises 4 to 30 and preferably 8 to 30 carbon atoms. It is preferably chosen from hexanoic acid, heptanoic acid, octanoic acid, ethyl-2 hexanoic acid, nonanoic acid, decanoic acid, undecanoic acid, dodecanoic acid, tridecanoic acid, tetradecanoic acid, pentadecanoic acid, hexadecanoic acid, hexyldecanoic acid, heptadecanoic acid, octadecanoic acid, isostearic acid, nonadecanoic acid, eicosanoic acid, isoarachidic acid, octyldodecanoic acid, heneicosanoic acid, docosanoic acid, and mixtures thereof. The aliphatic carboxylic acid is preferably branched. The aliphatic hydroxy carboxylic acid ester is advantageously derived from a hydroxylated aliphatic carboxylic acid comprising 2 to 40 carbon atoms, preferably 10 to 34 carbon atoms and more preferably 12 to 28 carbon atoms, and 1 to 20 hydroxyl groups, preferably 1 to 10 hydroxyl groups and more preferably 1 to 6 hydroxyl groups. The aliphatic hydroxy carboxylic acid ester is chosen from:

a) partial or total esters of saturated, linear mono-hydroxylated aliphatic monocarboxylic acids;

b) partial or total esters of unsaturated, linear mono-hydroxylated aliphatic monocarboxylic acids;

c) partial or total esters of saturated non-hydroxylated aliphatic carboxylic polyacids;

d) partial or total esters of saturated poly-hydroxylated aliphatic carboxylic polyacids;

e) partial or total esters in $C_2$ to $C_{16}$ of aliphatic polyol, having reacted with a mono or poly-hydroxylated aliphatic mono or polycarboxylic acid, and mixtures thereof.

dimer diol and dimer diacid esters, optionally esterified on the alcohol or free acid function(s) thereof by acid or alcohol radicals, particularly dimer dilinoleate esters, such esters may particularly be chosen from esters having the following INCI classification: bis-behenyl/isostearyl/phytosteryl dimerdilinoleyl dimerdilinoleate (Plandool G), phytosteryl/isosteryl/cetyl/stearyl/behenyl dimerdilinoleate (Plandool H or Plandool S), and mixtures thereof, butters of plant origin, such as mango butter, such as the one sold under the reference Lipex 203 by AARHUSKARLSHAMN, shea butter, in particular the one of which the INCI name is Butyrospermum Parkii Butter, such as the one sold under the reference Sheasoft® by AARHUSKARLSHAMN, cupuacu butter (Rain forest RF3410 from Beraca Sabara), murumuru butter (RAIN FOREST RF3710 from Beraca Sabara), cocoa butter as well as orange wax such as, for example, the one sold under the reference Orange Peel Wax by Koster Keunen, totally or partially hydrogenated plant oils, such as for example hydrogenated soybean oil, hydrogenated coconut oil, hydrogenated rapeseed oil, mixtures of hydrogenated plant oils such as the mixture of hydrogenated plant oil of soybean, coconut, palm and rapeseed, for example the mixture sold under the reference Akogel® by AARHUSKARLSHAMN (INCI name Hydrogenated Vegetable Oil), trans isomerized partially hydrogenated jojoba oil manufactured or sold by Desert Whale under the commercial reference Iso-Jojoba-50®, partially hydrogenated olive oil such as, for example, the compound sold under the reference Beurrolive by Soliance, hydrogenated castor oil esters, such as dimer dilinoleate hydrogenated castor oil for example RISOCAST-DA-L sold by KOKYU ALCOHOL KOGYO, hydrogenated castor oil isostearate for example SALACOS HCIS (V-L) sold by NISSHIN OIL, and mixtures thereof.

Among the pasty compounds, preferable choice will be given to liposoluble polyethers, esters and polyesters with more particularly glycerol oligomer esters, and preferably bis-diglyceryl polyacyladipate-2 (INCI name), butters of plant origin, totally or partially hydrogenated plant oils.

According to the invention, the preferred pasty compounds are chosen from vaseline, esters and polyesters, and more particularly glycerol oligomer esters, such as bis-diglyceryl polyacyladipate-2 (INCI name), and butters of plant origin, as well as mixtures thereof.

Alkylcellulose

The compositions of the invention can further comprise alkylcellulose, of which the alkyl portion is in $C_2$-$C_6$, preferably in $C_2$-$C_3$, in particular ethylcellulose, preferable with a content less than 10% by weight of active substance, in relation to the total weight of said composition.

Preferably, the alkylcellulose is chosen from ethylcellulose, propylcellulose, and in accordance with a very particularly advantageous embodiment, the alkylcellulose is ethylcellulose.

The alkylcellulose is a cellulose $C_2$-$C_6$ aliphatic ether, in particular ethyl ether in the case of ethylcellulose, comprising a chain comprised of β-anhydroglucose units bonded together by acetal bonds. Each anhydroglucose unit has thee replaceable hydroxyl groups, all or a portion of these hydroxyl groups can react according to the following reaction:

$RONa+R'Cl \rightarrow ROR'+NaCl$, where R is a cellulose radical and R' a $C_2$-$C_6$, preferably $C_2H_5$, alkyl radical.

The total substitution of the three hydroxyl groups would result for each anhydroglucose unit to a degree of substitution of 3, in other words to an alkoxy group content, in particular ethoxy of 54.88%.

The alkylcellulose polymers, in particular ethylcellulose, used in a cosmetic composition according to the invention are preferably polymers that have a degree of substitution in alkoxy groups, preferably ethoxy, ranging from 2.5 to 2.6 per anhydroglucose unit, in other words comprising a content in alkoxy groups, preferably ethoxy ranging from 44% to 50%.

In particular, the alkylcellulose implemented during the preparation of a composition according to the invention, can have the form of a powder.

If the composition contains any, the content in ethylcellulose is between 0.1% and 2.5% by weight, preferably between 0.5% and 2% by weight, expressed as the active material of alkylcellulose, in relation to the weight of the composition.

Aqueous Phase

The composition according to the invention comprises an aqueous phase, which forms the dispersed phase of the composition.

According to an embodiment, the compositions according to the invention comprise 15% to 70% by weight, preferably 20% to 60% by weight of water, with respect to the total weight of the composition.

Preferably, the compositions of the invention comprise more than 30% by weight, even more than 35% by weight of water in relation to the total weight of said composition.

In addition to water, the aqueous phase can also comprise at least one water-soluble solvent.

The term "water-soluble solvent" in the present invention denotes a compound that is liquid at ambient temperature and water-miscible (miscibility in water greater than 50% by weight at 25° C. and atmospheric pressure).

The water-soluble solvents suitable for use in the compositions according to the invention may further be volatile.

Among the water-soluble solvents that can be used in the compositions in accordance with the invention, mention can be made in particular of monoalcohols having from 1 to 5 carbon atoms such as ethanol and isopropanol, $C_3$ and $C_4$ ketones and $C_2$-$C_4$ aldehydes, and preferably monoalcohols having from 1 to 5 carbon atoms such as ethanol and isopropanol.

Preferably, the composition according to the invention preferably comprises a total content in mono-alcohols comprising between 2 and 8 carbon atoms between 0 and 15% by weight (limits included) in relation to the total weight of the composition.

Preferably, the composition according to the invention comprises a total content in mono-alcohols comprising between 2 and 8 carbon atoms between 0 and 10% by weight (limits included), advantageously between 0 and 5% by weight (limits included), in relation to the total weight of the composition.

$C_2$-$C_8$ Polyol

The composition may also comprise at least one $C_2$-$C_8$, preferably $C_3$-$C_6$, polyol, saturated or not, linear or branched, comprising from 2 to 6 hydroxyl groups.

Preferably the polyol is chosen from glycerin, propylene glycol, 1,3-butylene glycol and dipropylene glycol, tripropylene glycol, diglycerin, and mixtures thereof.

Preferably, the polybutene content represents from 0.05% to less than 10% by weight, particularly from 0.1% to less than 10% by weight, and more preferably from 1% to 6% by weight, with respect to the weight of the composition.

Dyes

According to one embodiment, the composition according to the invention can furthermore contain at least one coloring agent that can be chosen from water-soluble or liposoluble colorants, pigments, nacres and mixtures thereof.

The composition according to the invention can further comprise one or a plurality of dyes chosen from water-soluble or liposoluble colorants, and powder dyes such as pigments, nacres and glitter well known to those skilled in the art. The dyes may be present, in the composition, at a content ranging from 0.01% to 25% by weight, with respect to the weight of the composition, preferably from 0.01% to 20% by weight.

The term "colorants" refers to generally organic compounds soluble in fats such as oils or in an aqueous or hydroalcoholic phase.

The water-soluble dyes implemented according to the invention are more particularly water-soluble colorants.

The term "water-soluble colorant" refers to in terms of the invention, any generally organic, natural or synthetic compound, soluble in an aqueous phase or water-miscible solvents and able to dye. In particular, the term water-soluble is intended to characterize the aptitude of a compound to be solubilized in water, measured at 25° C., at a concentration at least equal to 0.1 g/l (obtaining of a macroscopically isotropic and transparent solution, colored or not). This solubility is in particular greater than or equal to 1 g/l.

In terms of water-soluble colorants that are suitable for the invention mention can in particular be made of synthetic or natural water-soluble colorants such as for example FDC Red 4 (CI: 14700), DC Red 6 (Lithol Rubine Na; CI: 15850), DC Red 22 (CI: 45380), DC Red 28 (CI: 45410 Na salt), DC Red 30 (CI: 73360), DC Red 33 (CI: 17200), DC Red 40 (CI: 16035), DC Orange 4 (CI: 15510), FDC Yellow 5 (CI: 19140), FDC Yellow 6 (CI: 15985), DC Yellow 8 (CI: 45350 Na salt), FDC Green 3 (CI: 42053), DC Green 5 (CI: 61570), FDC Blue 1 (CI: 42090).

Given by way of illustration and not limiting of sources of water-soluble dye(s) that can be implemented in the framework of this invention, mention can in particular be made of those of natural origin, such as extracts of carmine, cochineal, beet, grape, carrot, tomato, rocou, paprika, henna, caramel and curcumin.

As such, the water-soluble dyes that are suitable for the invention are in particular carminic acid, betanin, anthocyanins, enocyanins, lycopene, beta-carotene, bixin, norbixin, capsanthyn, capsorubin, flovoxanthin, lutein, cryptoxanthin, rubixanthin, violaxanthin, riboflavin, roudoxanthin, cantaxanthin, chlorophyll, and mixtures thereof.

It can also be copper sulfate, iron, water-soluble sulfopolyesters, rhodamine, betaine, methylene blue, disodium tartrazine salt and disodium fuchsin salt.

Some of these water-soluble dyes are in particular approved from a food standpoint. By way of example of these colorants, more particular mention can be made of the colorants in the carotenoid family, referenced under food codes E120, E162, E163, E160a-g, E150a, E101, E100, E140 and E141.

According to a particularly preferred embodiment, the water-soluble dye(s) are chosen from the sodium salts of Yellow 6, Yellow 5, Red 6, Red 33, Red 40.

Among the liposoluble colorants, particular mention can be made of Sudan Red, DC Red 17, DC Green 6, β-carotene, Sudan Brown, DC Yellow 11, DC Violet 2, DC Orange 5, Quinoline Yellow, Red 21, Red 22, Red 27, Red 28.

The term "pigments" should be understood to mean white or colored, mineral or organic particles, which are insoluble in an aqueous solution and are intended for coloring and/or opacifying the resulting film.

The pigments may be present in a proportion of 0.01% to 25% by weight, in particular from 0.01% to 20% by weight, with respect to the total weight of the cosmetic composition. The pigments can be chosen from mineral pigments, organic pigments, and composite pigments (i.e. pigments with a mineral and/or organic material base).

The pigments can be chosen from monochrome pigments, lacquers, nacres, pigments with an optical effect, such as reflective pigments and goniochromatic pigments.

Mineral pigments can be chosen from metal oxide pigments, chromium oxides, iron oxides, titanium oxide, zinc oxides, cerium oxides, zirconium oxides, manganese violet, Prussian blue, ultramarine blue, ferric blue, and mixtures thereof.

It can also be a pigment having a structure that may be, for example, of sericite/brown iron oxide/titanium dioxide/silica type. Such a pigment is marketed, for example, under the reference COVERLEAF NS or JS by CHEMICALS AND CATALYSTS and has a contrast ratio of around 30.

The dye may also comprise a pigment having a structure that may, for example, be of the type of silica microspheres containing iron oxide. An example of a pigment having this structure is marketed by MIYOSHI under the name PC BALL PC-LL-100 P, and this pigment consists of silica microspheres containing yellow iron oxide.

The organic pigments can for example be:
cochineal carmine,
organic pigments with azoic, anthraquinonic, indigoid, xanthenic, pyrenic, quinolinic, triphenylmethane, fluorane colorants;
organic lacquers or insoluble salts of sodium, of potassium, of calcium, of barium, of aluminum, of zirconium, of strontium, of titanium, of acid colorants such as the azoic, anthraquinonic, indigoid, xanthenic, pyrenic, quinolinic, triphenylmethane, fluorane colorants. These colorants generally contain at least one carboxylic or sulfonic acid group;
melanic pigments.

Among the organic pigments, mention can be made of D&C Blue no. 4, D&C Brown no. 1, D&C Green no. 5, D&C Green no. 6, D&C Orange no. 4, D&C Orange no. 5, D&C Orange no. 10, D&C Orange no. 11, D&C Red no. 7 (Calcium salt of Lithol Rubine), D&C Red no. 17, D&C Red no. 21, D&C Red no. 22, D&C Red no. 27, D&C Red no. 28, D&C Red no. 30, D&C Red no. 31, D&C Red no. 33, D&C Red no. 34, D&C Red no. 36, D&C Violet no. 2, D&C Yellow no. 7, D&C Yellow no. 8, D&C Yellow no. 10, D&C Yellow no. 11, FD&C Blue no. 1, FD&C Green no. 3, FD&C Red no. 40, FD&C Yellow no. 5, FD&C Yellow no. 6.

Along the organic lacquers, mention can be made of organic lacquers supported by an organic support such as colophony or aluminum benzoate, for example. Preferably, among the organic lacquers, mention can in particular be made of those known under the following names: D&C Red no. 2 Aluminum lake, D&C Red no. 3 Aluminum lake, D&C Red no. 4 Aluminum lake, D&C Red no. 6 Aluminum lake, D&C Red no. 6 Barium lake, D&C Red no. 6 Barium/ Strontium lake, D&C Red no. 6 Strontium lake, D&C Red no. 6 Potassium lake, D&C Red no. 7 Aluminum lake, D&C Red no. 7 Barium lake, D&C Red no. 7 Calcium lake, D&C Red no. 7 Calcium/Strontium lake, D&C Red no. 7 Zirconium lake, D&C Red no. 8 Sodium lake, D&C Red no. 9 Aluminum lake, D&C Red no. 9 Barium lake, D&C Red no. 9 Barium/Strontium lake, D&C Red no. 9 Zirconium lake, D&C Red no. 10 Sodium lake, D&C Red no. 19 Aluminum lake, D&C Red no. 19 Barium lake, D&C Red no. 19 Zirconium lake, D&C Red no. 21 Aluminum lake, D&C Red no. 21 Zirconium lake, D&C Red no. 22 Aluminum lake, D&C Red no. 27 Aluminum lake, D&C Red no. 27 Aluminum/Titanium/Zirconium lake, D&C Red no. 27 Barium lake, D&C Red no. 27 Calcium lake, D&C Red no. 27 Zirconium lake, D&C Red no. 28 Aluminum lake, D&C Red no. 30 lake, D&C Red no. 31 Calcium lake, D&C Red no. 33 Aluminum lake, D&C Red no. 34 Calcium lake, D&C Red no. 36 lake, D&C Red no. 40 Aluminum lake, D&C Blue no. 1 Aluminum lake, D&C Green no. 3 Aluminum lake, D&C Orange no. 4 Aluminum lake, D&C Orange no. 5 Aluminum lake, D&C Orange no. 5 Zirconium lake, D&C Orange no. 10 Aluminum lake, D&C Orange no. 17 Barium lake, D&C Yellow no. 5 Aluminum lake, D&C Yellow no. 5 Zirconium lake, D&C Yellow no. 6 Aluminum lake, D&C Yellow no. 7 Zirconium lake, D&C Yellow no. 10 Aluminum lake, FD&C Blue no. 1 Aluminum lake, FD&C Red no. 4 Aluminum lake, FD&C Red no. 40 Aluminum lake, FD&C Yellow no. 5 Aluminum lake and FD&C Yellow no. 6 Aluminum lake.

The pigments can be treated by a hydrophobic agent.

The hydrophobic treatment agent can be chosen from silicones such as methicones, dimethicones, perfluoroalkylsilanes; fatty acids such as stearic acid; metallic soaps such as aluminum dimyristate, the aluminum salt of hydrogenated tallow glutamate, perfluoroalkyl phosphates, perfluoroalkyl silanes, perfluoroalkyl silazanes, hexafluoropropylene polyoxides, polyorganosiloxanes comprising perfluoroalkyl perfluoropolyethers groups, amino acids; N-acylated amino acids or salts thereof; lecithin, isopropyl triisostearyl titanate and mixtures thereof.

The N-acylated amino acids may comprise an acyl group having 8 to 22 carbon atoms, such as for example a 2-ethyl hexanoyl, caproyl, lauroyl, myristoyl, palmitoyl, stearoyl, cocoyl group. The salts of these compounds may be aluminum, magnesium, calcium, zirconium, zinc, sodium, potassium salts. The amino acid may be for example lysine, glutamic acid, alanine.

The term alkyl mentioned in the above-mentioned compounds particularly denotes an alkyl group having 1 to 30 carbon atoms, preferably having 5 to 16 carbon atoms.

Hydrophobic treated pigments are in particular described in application EP-A-1086683.

The term "nacres" should be understood to mean iridescent or non-iridescent colored particles of any shape which are in particular produced by certain mollusks in their shell or else are synthesized and which exhibit a color effect by optical interference.

The nacres may be selected from pearlescent pigments such as titanium mica coated with iron oxide, titanium mica coated with bismuth oxychloride, titanium mica coated with chromium oxide, titanium mica coated with an organic dye, and pearlescent pigments based on bismuth oxychloride. This may also involve mica particles at the surface whereof are superposed at least two successive layers of metal oxides and/or of organic dyes.

By way of example of nacres, mention may also be made of natural mica coated with titanium oxide, with iron oxide, with natural pigment or with bismuth oxychloride.

Among the nacres available on the market, mention may be made of the TIMICA, FLAMENCO and DUOCHROME nacres (based on mica) marketed by ENGELHARD, the TIMIRON nacres marketed by MERCK, the nacres based on mica, PRESTIGE, marketed by ECKART and the nacres based on synthetic mica, SUNSHINE, marketed by SUN CHEMICAL.

The nacres may more particularly possess a yellow, pink, red, bronze, orange, brown, gold and/or copper color or glint.

By way of illustration of nacres which can be used in the context of the invention, mention may, in particular, be made of the gold nacres marketed, in particular, by ENGELHARD, under the name Brilliant gold 212G (Timica), Gold 222C (Cloisonne), Sparkle gold (Timica), Gold 4504 (Chromalite) and Monarch gold 233X (Cloisonne); the bronze nacres, marketed, in particular, by MERCK under the name Bronze fine (17384) (Colorona) and Bronze (17353) (Colorona) and by ENGELHARD under the name Super bronze (Cloisonne); the orange nacres, in particular, marketed by ENGELHARD under the name Orange 363C (Cloisonne) and Orange MCR 101 (Cosmica) and by MERCK under the name Passion orange (Colorona) and Matte orange (17449) (Microna); the brown-hued nacres marketed in particular by ENGELHARD under the name Nu-antique copper 340X6 (Cloisonne) and Brown CL4509 (Chromalite); the copper-glint nacres marketed in particular by ENGELHARD under the name Copper 340A (Timica); the red-glint nacres marketed in particular by MERCK under the name Sienna fine (17386) (Colorona); the yellow-glint nacres marketed in particular by ENGELHARD under the name Yellow (4502) (Chromalite); the gold-glint red-hued nacres marketed in particular by ENGELHARD under the name Sunstone G012 (Gemtone); the pink nacres marketed in particular by ENGELHARD under the name Tan opal G005 (Gemtone); the gold-glint black nacres marketed in particular by ENGELHARD under the name Nu-antique bronze 240 AB (Timica), the blue nacres marketed in particular by MERCK under the name Matte blue (17433) (Microna), the silver-glint white nacres marketed in particular by MERCK under the name Xirona Silver and the green-gold and pinkish orangish nacres marketed in particular by MERCK under the name Indian summer (Xirona) and mixtures thereof.

The cosmetic composition according to the invention may also contain at least one material with a specific optical effect.

This effect is different from a simple conventional hue effect, i.e. a unified and stabilized effect of the kind produced by conventional dyes, such as, for example, monochromatic pigments. For the purpose of the invention, the term "stabilized" signifies absence of an effect of variability of color with the angle of observation or in response to a temperature change.

For example, this material may be selected from particles having a metallic glint, goniochromatic coloring agents, diffracting pigments, thermochromatic agents, optical brighteners, and also fibers, in particular of the interference type. Of course, these various materials may be combined so as to provide the simultaneous manifestation of two effects, or even a new effect in accordance with the invention.

The metallic-glint particles that can be used in the invention are in particular chosen from:
 particles of at least one metal and/or of at least one metal derivative, particles comprising a single-substance or multi-substance, organic or mineral substrate, at least partially coated with at least one metallic-glint layer comprising at least one metal and/or at least one metal derivative, and mixtures of said particles.

Among the metals that may be present in said particles, mention may, for example, be made of Ag, Au, Cu, Al, Ni, Sn, Mg, Cr, Mo, Ti, Zr, Pt, Va, Rb, W, Zn, Ge, Te, Se and mixtures or alloys thereof. Ag, Au, Cu, Al, Zn, Ni, Mo, Cr and mixtures or alloys thereof (for example, bronzes and brasses) are preferred metals.

The term "metal derivatives" denotes compounds derived from metals, in particular oxides, fluorides, chlorides and sulfides By way of illustration of these particles, mention may be made of aluminum particles, such as those marketed under the trade names STARBRITE 1200 EAC® by SIBERLINE and METALURE® by ECKART.

Mention may also be made of metal powders of copper or of alloy mixtures, such as the references 2844 marketed by RADIUM BRONZE, metal pigments, such as aluminum or bronze, for instance those marketed under the trade name ROTOSAFE 700 by ECKART, silica-coated aluminum particles marketed under the trade name VISIONAIRE BRIGHT SILVER bye ECKART and metal alloy particles, such as silica-coated bronze (copper and zinc alloy) marketed under the trade name Visionaire Bright Natural Gold by Eckart.

The particles in question may also be particles comprising a glass substrate, such as those marketed by NIPPON SHEET GLASS under the trade name MICROGLASS METASHINE.

The goniochromatic coloring agent may be selected, for example, from multilayer interference structures and liquid-crystal coloring agents.

Examples of symmetrical multilayer interference structures that may be used in compositions prepared according to the invention are, for example, the following structures: $Al/SiO_2/Al/SiO_2/Al$, pigments having this structure being marketed by DUPONT DE NEMOURS; $Cr/MgF_2/Al/MgF_2/Cr$, pigments having this structure being marketed under the trade name CHROMAFLAIR by FLEX; $MoS_2/SiO_2/Al/SiO_2/MoS_2$; $Fe_2O_3/SiO_2/Al/SiO_2/Fe_2O_3$, and $Fe_2O_3/SiO_2/Fe_2O_3/SiO_2/Fe_2O_3$, pigments having these structures being marketed under the trade name SICOPEARL by BASF; $MoS_2/SiO_2/mica$-$oxide/SiO_2/MoS_2$; $Fe_2O_3/SiO_2/mica$-$oxide/SiO_2/Fe_2O_3$; $TiO_2/SiO_2/TiO_2$ and $TiO_2/Al_2O_3/TiO_2$; $SnO/TiO_2/SiO_2/TiO_2/SnO$; $Fe_2O_3/SiO_2/Fe_2O_3$; $SnO/mica/TiO_2/SiO_2/TiO_2/mica/SnO$, pigments having these structures being marketed under the trade name XIRONA by MERCK (Darmstadt). By way of example, these pigments may be the pigments with a silica/titanium oxide/tin oxide structure marketed under the name XIRONA MAGIC by MERCK, pigments with a silica/brown iron oxide structure marketed under the name XIRONA INDIAN SUMMER by MERCK and pigments with a silica/titanium oxide/mica/tin oxide structure marketed under the name XIRONA CARRIBEAN BLUE by MERCK. Mention may also be made of the INFINITE COLORS pigments from SHISEIDO. Depending on the thickness and the nature of the various layers, various effects are obtained. Thus, with the structure $Fe_2O_3/SiO_2/Al/SiO_2/Fe_2O_3$, the color changes from green-golden to red-gray for $SiO_2$ layers from 320 to 350 nm; from red to golden for $SiO_2$ layers from 380 to 400 nm; from violet to green for $SiO_2$ layers from 410 to 420 nm; from copper to red for $SiO_2$ layers from 430 to 440 nm.

By way of example of pigments with a polymeric multilayer structure, mention may be made of those marketed by 3M under the trade name COLOR GLITTER.

Examples of liquid-crystal goniochromatic particles that may be used include those sold by CHENIX, and also that marketed under the trade name HELICONE® HC by WACKER.

Usual Additional Cosmetic Ingredients

The composition according to the invention can further comprise any usual cosmetic ingredient that can be chosen in particular from the hydrophobic thickeners, fillers of an organic or mineral nature, antioxidants, anti-UV filters, perfumes, preservatives, neutralizers, sequestrants, film-forming agents, active ingredients, and mixtures thereof.

Obviously, those skilled in the art will take care to choose these optional additional ingredients, and/or the quantity thereof, such that the advantageous properties of the active constituents of the composition according to the invention are not, or are substantially not, altered by the envisaged addition.

The hydrophobic thickener can be chosen from alkylated guar gums (with a C1-C6 alkyl group), such as those described in EP708114; oil gelling agent polymers such as triblock polymers or as a star resulting from the polymerization or copolymerization of at least one monomer with an ethylene group, such as the polymers sold under the name Kraton; resins of polyamides comprising alkyl groups having from 12 to 22 carbon atoms, such as those described in U.S. Pat. No. 5,783,657; polysaccharide alkylethers, in particular of which the alkyl group comprises from 1 to 24 carbon atoms, preferably from 1 to 10, better from 1 to 6, and more specifically from 1 to 3, such as those described in document EP-A-898958; organophilic clays; hydrophobic pyrogenic silicas; hydrophobic silica aerogels; elastomeric organopolysiloxanes and mixtures thereof.

The clays are silicates that contain a cation that can be chosen from the cations of calcium, magnesium, aluminum, sodium, potassium, lithium and mixtures thereof. As examples of such products, mention can be made of clays of the family of smectites such as montmorillonites, hectorites, bentonites, beidellites, saponites, as well as of the family of vermiculites, stevensite, chlorites. These clays may be of natural or synthetic origin. Organophilic clays are clays modified with a chemical compound chosen from the quaternary amines, tertiary amines, acetate amines, imidazolines, amine soaps, fatty sulfates, alkyl aryl sulfonates, amide oxides, and mixtures thereof.

Mention can as such be made of hectorites modified by a quaternary amine, more precisely by a halide, such as a $C_{10}$ to $C_{22}$ fatty acid ammonium chloride, such as hectorite modified by di-stearyl di-methyl ammonium chloride (CTFA name: Disteardimonium hectorite), such as, for example, the one sold under the name Bentone 38V®, Bentone 38V CG, Bentone EW CE, by ELEMENTIS; the stearalkonium Hectorites such as Bentone 27 V.

Mention can also be made of quaternium-18 bentonites such as those sold under the names Bentone 34 sold by Elementis, Claytone 40, Tixogel VP by United catalyst by Southern Clay; stearalkonium bentonites such as those sold under the names Tixogel LG by United Catalyst, Claytone AF, Claytone APA by Southern Clay; quaternium-18/benzalkonium bentonite such as those sold under the name Claytone HT by Southern Clay According to a preferred embodiment, the thickening agent is chosen from modified organophilic clays, in particular modified organophilic hectorites, in particular by halides, preferably ammonium benzyldimethyl stearate, distearyl dimethyl ammonium chlorides.

The hydrophobic pyrogenic silicas can be obtained by modifying the surface of the silica by a chemical reaction that generates a decrease in the number of silanol groups, with these groups in particular able to be substituted with hydrophobic groups. The hydrophobic groups may be:

trimethylsiloxyl groups, particularly obtained by treating pyrogenic silica in the presence of hexamethyldisilazane. Silicas treated in this way are referred to as "Silica silylate" as per the CTFA (6th edition, 1995). They are for example sold under the references "AEROSIL R812®" by Degussa, "CAB-O-SIL TS-530®" by Cabot, dimethylsilyloxyl or polydimethylsiloxane groups, particularly obtained by treating pyrogenic silica in the presence of polydimethylsiloxane or dimethyldichlorosilane. Silicas treated in this way are referred to as "Silica dimethyl silylate" as per the CTFA (6th edition, 1995). They are for example sold under the references "AEROSIL R972®", "AEROSIL R974®" by Degussa, "CAB-O-SIL TS-610®", "CAB-O-SIL TS-720®" by Cabot.

The silica aerogels are porous materials obtained by replacing (via drying) the liquid component of a silica gel with air. They are generally synthesized by the sol-gel method in a liquid medium then dried usually via the extraction of a supercritical fluid, with the most commonly used being supercritical $CO_2$. This type of drying makes it possible to prevent the contraction of the pores and of the material. The sol-gel method and the various dryings are described in detail in Brinker C J., and Scherer G. W., Sol-Gel Science: New York: Academic Press, 1990.

Particles of hydrophobic silica aerogels modified on the surface by trimethylsilyl groups will preferably be used.

As hydrophobic silica aerogels, mention can be made for example of the aerogel sold under the name VM-2260 (INCI name Silica silylate), by Dow Corning, of which the particles have an average size of about 1000 microns and a specific area per unit mass ranging from 600 to 800 $m^2/g$. Mention can also be made of the aerogels sold by Cabot under the references AEROGEL TLD 201, AEROGEL OGD 201, AEROGEL TLD 203, ENOVA® AEROGEL MT 1100, ENOVA AEROGEL MT 1200.

The elastomeric organopolysiloxanes are in general partially or totally cross-linked and possibly of a three-dimensional structure. The elastomeric organopolysiloxanes associated with a fatty phase generally have the form of a gel comprised of an elastomeric organopolysiloxane associated with a fatty phase, included in at least one hydrocarbon oil and/or a silicone oil. They can be chosen in particular from the cross-linked polymers described in application EP-A-0295886. According to this application, the elastomeric organopolysiloxanes are obtained par by addition reaction and cross-linking of at least:

(a) an organopolysiloxane having at least two lower alkenyl groups per molecule;
(b) an organopolysiloxane having at least two hydrogen atoms bound to a silicon atom per molecule; and
(c) and a catalyst of the platinum type.

The additional thickening agent may be present at a content ranging from 0.1% to 10% by weight, in relation to the total weight of the preferably ranging from 0.1% to 5% by weight.

The term "filler" should be understood to mean colorless or white solid particles of any shape, which are in a form that is insoluble or dispersed in the medium of the composition. They are separate from the dyes.

Among the fillers that can be used in the compositions according to the invention, mention can be made of silica, kaolin, starch, lauroyl-lysine, mica, talc, sericite, polyamide powders (Nylon®), poly-p-alanine and polyethylene, powders of tetrafluoroethylene polymers (Teflon®), the polymeric hollow microbeads such as those of polyvinylidene/acrylonitrile chloride such as Expancel® (Nobel Industrie), of copolymers of acrylic acid, silicone resin microbeads (Tospearls® from Toshiba, for example), elastomer polyorganosiloxane particles, precipitated calcium carbonate, magnesium carbonate and hydro-carbonate, hydroxyapatite, barium sulfate, aluminum oxides, polyurethane powders, composite fillers, hollow silica microbeads, glass or ceramic microcapsules, metallic soaps derived from carboxylic organic acids having 8 to 22 carbon atoms, preferably from 12 to 18 carbon atoms, for example zinc, magnesium or lithium stearate, zinc laurate, magnesium myristate and mixtures thereof.

A composition implemented according to the invention may comprise one or more fillers at a content ranging from 0.1% to 5% by weight, with respect to the weight of the composition.

Humectant or Moisturizing Agent

According to an embodiment, the compositions of the invention further comprise a humectant or moisturizing agent, different from the aforementioned polyols.

As humectant or moisturizing agents, mention can be made in particular of sugars such as sorbitol or xylitol; hyaluronic acid and the salts thereof, beads of hyaluronic acid such as those sold by Engelhard Lyon; AHA, BHA, and for example lactic acid and the salts thereof, in particular alkaline metal, such as sodium lactate; serine, arginine; ectoine and the derivatives thereof; chitosan and the derivatives thereof; collagen, collagen and chondroitin sulfate beads and of marine origin (Ateocollagen) sold by Engelhard Lyon under the name marine filling beads; beta-glucan and in particular sodium carboxymethyl beta-glucane from Mibelle-AG-Biochemistry, a C-glycoside derivative such as those described in application WO 02/051828 and in particular CβDxylopyranoside2hydroxypropane in the form of a 30% solution by weight in active material in a water/propylene glycol mixture (60/40% by weight) such as the product manufactured by CHIMEX under the trade name "MEXORYL SBB®"; plant extracts in an aqueous or oily medium such as in particular pomegranate extract, the aqueous solutions obtained using *Cocos nucifera*; sphingolipids, such as ceramide 5; as well as mixtures thereof.

Preferably, humectant or moisturizing agent or agents are chosen from sugars such as sorbitol, xylitol; hyaluronic acid and the salts thereof, AHA, BHA, in particular lactic acid and the sodium salts thereof; serine, arginine; ectoine and the derivatives thereof; chitosan and the derivatives thereof, collagen, collagen and chondroitin sulfate beads and of marine origin; and beta-glucan; plant extracts in an aqueous or oily medium such as in particular pomegranate extract, the aqueous solutions obtained using *Cocos nucifera*; sphingolipids; as well as mixtures thereof.

A composition according to the invention can furthermore comprise any additional component usually used in cosmetics, such as dyes, fillers or cosmetic active ingredients.

Obviously, those skilled in the art will take care to choose the optional additional compounds, and/or the quantity thereof, such that the advantageous properties of the composition used according to the invention are not, or are substantially not, altered by the envisaged addition.

The composition according to the invention is obviously a cosmetic composition, therefore comprising a physiologically acceptable medium.

The term "physiologically acceptable medium" is intended to denote a medium that is particularly suitable for the application of a composition of the invention to the skin, in particular to the lips.

The physiologically acceptable medium is generally suitable for the nature of the support to which the composition should be applied, and also for the way in which the composition is to be packaged.

The invention also relates to a non-therapeutic makeup and/or care for the lips including a step for applying on the lips of a cosmetic composition such as defined hereinabove.

The examples hereinafter are given by way of illustration and are not intended to restrict this invention. The percentages are percentages by weight.

EXAMPLES

Example 1

The composition is prepared of which the ingredients are listed in the table hereinbelow (the percentages are expressed by weight of raw material unless mentioned otherwise).

|  | Ingredients (INCI name) | Content (% weight) |
|---|---|---|
| Oily phase | DIMETHICONE (and) PEG/PPG-18/18 DIMETHICONE X-22-6711D from Shin Etsu | 7 |
|  | Phenyl trimethicone (Dow Corning 556 cosmetic Grad Fluid, Dow Corning) | 10 |
|  | *Prunus armeniaca* (apricot) kernel oil (Refined Apricot Kernel oil, Olvea) | 7 |
|  | petrolatum (ULTIMA WHITE PET USP; calumet Specialty) | 5 |
|  | Hydrogenated Polyisobutene (Polysynlane V, NOF corporation) | 3 |
|  | Tocopheryl acetate | 0.5 |
|  | Disteardimonium hectorite (Bentone VCG, Elementis) | 0.5 |
|  | propylene carbonate | 0.07 |
|  | POLYGLYCERYL-3 BEESWAX (CERA BELLINA E00022; Koster Keunen) | 7 |
| Aqueous phase | glycerin | 6 |
|  | propylene glycol | 2 |
|  | water | qs 100% |
|  | preservative | 0.5 |

Procedure:

The disteardimonium hectorite is mixed in the apricot oil and the propylene carbonate in the Rayneri deflloculator.

The oily phase is prepared by mixing all of the ingredients in a double-shell skillet and once the mixture is homogenized, the previously-obtained bentone gel is added therein.

This is homogenized and the wax is added at 80° C. and the whole is homogenized in the Rayneri defflloculator.

Separately, the aqueous phase is prepared by mixing the ingredients under stirring in the Rayneri defflloculator and the temperature is stabilized to 60° C.

The emulsion is then prepared by slowly pouring the aqueous phase obtained as such, over the preceding fatty phase (stirring in the Morritz; 3,000 to 4,000 rpm).

The mixture obtained is cooled to ambient temperature under stirring (butterfly blades).

The composition is cooled to ambient temperature and conditioned in a suitable container.

Results:

A homogeneous and stable composition is obtained.

The composition is easy to apply, in a homogeneous deposit that does not flow and that does not chase.

The deposit is fresh, thin, is not tacky and procures a persistent moisturizing effect.

Example 2

The composition is prepared of which the ingredients are listed in the table hereinbelow (the percentages are expressed by weight of raw material unless mentioned otherwise).

|  | Ingredients (INCI name) | Content (% weight) |
|---|---|---|
| Oily phase | DIMETHICONE (and) PEG/PPG-18/18 DIMETHICONE X-22-6711D from Shin Etsu | 7 |
|  | Phenyl trimethicone (Dow Corning 556 cosmetic Grad Fluid, Dow Corning) | 6 |
|  | *Prunus armeniaca* (apricot) kernel oil (Refined Apricot Kernel oil, Olvea) | 7 |
|  | petrolatum (ULTIMA WHITE PET USP; calumet Specialty) | 4 |
|  | BIS-DIGLYCERYL POLYACYLADIPATE-2 (Softisan 649, Cremer Oleo) | 5 |
|  | Hydrogenated Polyisobutene (Polysynlane V, NOF corporation) | 5 |
|  | tocopheryl acetate | 0.5 |
|  | Disteardimonium hectorite | 0.5 |

|  | Ingredients (INCI name) | Content (% weight) |
|---|---|---|
| Aqueous phase | (Bentone VCG, Elementis) propylene carbonate | 0.07 |
|  | POLYGLYCERYL-3 BEESWAX (CERA BELLINA E00022; Koster Keunen) | 3 |
|  | glycerin | 8 |
|  | water | qs 100% |
|  | ETHYLCELLULOSE Aquacoat ECD 30; FMC Corporation; 30% dispersion in water, cetyl alcohol, sodium lauryl sulfate) | 7 |
|  | preservative | 0.5 |

Procedure:

The disteardimonium hectorite is mixed in the apricot oil and the propylene carbonate in the Rayneri deffloculator.

The remaining ingredients of the oily phase is then added to the previous mixture, under mixing, in a double-shell skillet at 80° C.

The whole is homogenized in the Rayneri deffloculator.

Separately, the aqueous phase is prepared by mixing the ingredients (except for the Aquacoat ECD) under stirring in the Rayneri deffloculator and the temperature is stabilized to 60° C.

The emulsion is then prepared by slowly pouring the aqueous phase obtained as such, over the preceding fatty phase (stirring in the Morritz; 3,000 to 4,000 rpm).

The mixture obtained is cooled to ambient temperature under stirring (butterfly blades).

Finally at 50° C., the Aquacoat ECD is added under stirring.

The composition is cooled to ambient temperature and conditioned in an adapted container.

Results:

A homogeneous and stable composition is obtained.

The composition is easy to apply, in a homogeneous deposit that does not flow and that does not chase.

The deposit is fresh, thin, is not tacky and procures a persistent moisturizing effect.

Example 3

The composition is prepared of which the ingredients are listed in the table hereinbelow (the percentages are expressed by weight of raw material unless mentioned otherwise).

|  | Ingredients (INCI name) | Content (% weight) |
|---|---|---|
| A1 | Propylene carbonate | 0.2 |
|  | Pigments | 1.5 |
|  | Plant oils with a molecular weight greater than 400 Da | 13.7 |
|  | Disteardimonium hectorite (Bentone VCG, Elementis) | 0.7 |
| A2 | BIS-DIGLYCERYL POLYACYLADIPATE-2 (Softisan 649, Cremer Oleo) | 5.9 |
|  | Petrolatum (SNOW WHITE PET USP, from Calumet Specialty) | 3.9 |
|  | DIMETHICONE (and) PEG/PPG-18/18 DIMETHICONE X-22-6711D from Shin Etsu | 1.3 |
|  | CETYL PEG/PPG-10/1 DIMETHICONE (Abil EM 90, from Evonik Goldschmidt) | 3.9 |
|  | Cyclohexasiloxane | 3.9 |
|  | Phenyltrimethicone (DOW CORNING 556 COSMETIC GRADE FLUID, from Dow Corning) | 5.9 |
| A3 | POLYGLYCERYL-4 ISOSTEARATE (Isolan GI34, from Evonik Goldschmidt) | 1.3 |
|  | POLYGLYCERYL-3 BEESWAX (CERA BELLINA E00022; Koster Keunen) | 5.7 |
| A4 | Magnesium sulfate | 0.7 |
|  | Preservatives | 0.9 |
|  | Glycerin | 3 |
|  | Water | qs 100% |
| A5 | ETHYLCELLULOSE Aquacoat ECD 30; FMC Corporation; 30% dispersion in water, cetyl alcohol, sodium lauryl sulfate) | 5 |

Procedure:

The disteardimonium hectorite is mixed in the plant oils and the propylene carbonate in the Rayneri deffloculator.

The remaining ingredients of the oily phase are then added to the pprevious mixture under mixing in a double-shell skillet at 80° C.

The whole is homogenized in the Rayneri deffloculator.

Separately, the aqueous phase is prepared by mixing the ingredients (except for the Aquacoat ECD) under stirring in the Rayneri deffloculator and the temperature is stabilized to 60° C.

The emulsion is then prepared by slowly pouring the aqueous phase obtained as such, over the preceding fatty phase (stirring in the Morritz; 3,000 to 4,000 rpm).

The mixture obtained is cooled to ambient temperature under stirring (butterfly blades).

Finally at 50° C., the Aquacoat ECD is added under stirring.

The composition is cooled to ambient temperature and conditioned in an adapted container.

Results:

A homogeneous and stable composition is obtained.

The composition is easy to apply, in a homogeneous deposit that does not flow and that does not chase.

The deposit is fresh, thin, is not tacky and procures a persistent moisturizing effect.

Example 4

The composition is prepared of which the ingredients are listed in the table hereinbelow (the percentages are expressed by weight of raw material unless mentioned otherwise).

| | Ingredients (INCI name) | Content (% weight) |
|---|---|---|
| A1 | Propylene carbonate | 0.2 |
| | Pigments | 1.5 |
| | Refined apricot kernel oil (OLVEA) | 13.7 |
| | Disteardimonium hectorite (Bentone VCG, Elementis) | 0.7 |
| A2 | BIS-DIGLYCERYL POLYACYLADIPATE-2 (Softisan 649, Cremer Oleo) | 5.9 |
| | Petrolatum (SNOW WHITE PET USP, from Calumet Specialty) | 3.9 |
| | DIMETHICONE (and) PEG/PPG-18/18 DIMETHICONE X-22-6711D from Shin Etsu | 1.3 |
| | CETYL PEG/PPG-10/1 DIMETHICONE (Abil EM 90, from Evonik Goldschmidt) | 3.9 |
| | Cyclohexasiloxane | 3.9 |
| | Phenyltrimethicone (DOW CORNING 556 COSMETIC GRADE FLUID, from Dow Corning) | 5.9 |
| | POLYGLYCERYL-4 ISOSTEARATE (Isolan GI34, from Evonik Goldschmidt) | 1.3 |
| A3 | POLYGLYCERYL-3 BEESWAX (CERA BELLINA E00022; Koster Keunen) | 5.7 |
| A4 | Magnesium sulfate | 0.7 |
| | Preservatives | 0.9 |
| | Glycerin | 3 |
| | Water | qsp 100% |
| A5 | ETHYLCELLULOSE Aquacoat ECD 30; FMC Corporation; 30% dispersion in water, cetyl alcohol, sodium lauryl sulfate) | 5 |

Procedure:

Phase A1:

The disteardimonium hectorite is mixed in the apricot oil and the propylene carbonate in the Rayneri deffloculator.

The pigments are ground in this mixture in the 3-drum passage cylinder.

Phase A2:

The oily phase is prepared by mixing all of the ingredients of phase A2 in a double-shell skillet and once the mixture is homogenized, the previously obtained phase A1 is added therein.

This is homogenized and the wax is added at 80° C. (phase A3) and the whole is homogenized in the Rayneri deffloculator.

Separately, the aqueous phase is prepared by mixing the ingredients of phase A4 under stirring in the Rayneri deffloculator and the temperature is stabilized to 60° C.

The emulsion is then prepared by slowly pouring the aqueous phase obtained as such, over the preceding mixture (stirring in the Morritz; 3,000 to 4,000 rpm).

The mixture obtained is cooled to ambient temperature under stirring (butterfly blades).

Finally at 50° C., the Aquacoat ECD is added under stirring.

The composition is cooled to ambient temperature and conditioned in an adapted container.

Results:

A homogeneous and stable composition is obtained.

The viscosity of the composition is 6.2 Pa·s (as measured according to the protocol as described in the specification).

The composition is easy to apply, in a homogeneous deposit that does not flow and that does not chase. Moreover, it provides very good slippery properties and gives freshness sensation when applied on the lips.

The deposit is fresh, light, comfortable, shiny, and covering, without any lips tightness. It is not tacky and procures a persistent moisturizing effect, which keeps the lips hydrated, flexible, smooth, and soft.

This composition is stable for one month and two months, at several temperatures: 20° C., 4° C., and 45° C.

Example 5

The composition is prepared of which the ingredients are listed in the table hereinbelow (the percentages are expressed by weight of raw material unless mentioned otherwise).

| | Ingredients (INCI name) | Content (% weight) |
|---|---|---|
| A1 | Propylene carbonate | 0.2 |
| | Pigments | 1.5 |
| | Refined apricot kernel oil (OLVEA) | 13.7 |
| | Disteardimonium hectorite (Bentone VCG, Elementis) | 0.7 |
| A2 | BIS-DIGLYCERYL POLYACYLADIPATE-2 (Softisan 649, Cremer Oleo) | 5.9 |
| | Petrolatum (SNOW WHITE PET USP, from Calumet Specialty) | 3.9 |
| | DIMETHICONE (and) PEG/PPG-18/18 DIMETHICONE X-22-6711D from Shin Etsu | 1.3 |
| | CETYL PEG/PPG-10/1 DIMETHICONE (Abil EM 90, from Evonik Goldschmidt) | 3.9 |
| | Cyclohexasiloxane | 3.9 |
| | Phenyltrimethicone (DOW CORNING 556 COSMETIC GRADE FLUID, from Dow Corning) | 5.9 |
| | POLYGLYCERYL-4 ISOSTEARATE (Isolan GI34, from Evonik Goldschmidt) | 1.3 |
| A3 | BEESWAX (CERA ALBA; CERABEIL LOR from Baerlocher) | 5.7 |
| A4 | Magnesium sulfate | 0.7 |
| | Preservatives | 0.9 |
| | Glycerin | 3 |
| | Water | qsp 100% |
| A5 | ETHYLCELLULOSE Aquacoat ECD 30; FMC Corporation; 30% dispersion in water, cetyl alcohol, sodium lauryl sulfate) | 5 |

Procedure:

Phase A1:

The disteardimonium hectorite is mixed in the apricot oil and the propylene carbonate in the Rayneri deffloculator.

The pigments are ground in this mixture in the 3-drum passage cylinder.

Phase A2:

The oily phase is prepared by mixing all of the ingredients of phase A2 in a double-shell skillet and once the mixture is homogenized, the previously obtained phase A1 is added therein.

This is homogenized and the wax is added at 80° C. (phase A3) and the whole is homogenized in the Rayneri deffloculator.

Separately, the aqueous phase is prepared by mixing the ingredients of phase A4 under stirring in the Rayneri deffloculator and the temperature is stabilized to 60° C.

The emulsion is then prepared by slowly pouring the aqueous phase obtained as such, over the preceding mixture (stirring in the Morritz; 3,000 to 4,000 rpm).

The mixture obtained is cooled to ambient temperature under stirring (butterfly blades).

Finally at 50° C., the Aquacoat ECD is added under stirring.

The composition is cooled to ambient temperature and conditioned in an adapted container.

Results:

A homogeneous and stable composition is obtained.

The viscosity of the composition is 5.9 Pa·s (as measured according to the protocol as described in the specification).

The composition is easy to apply, in a homogeneous deposit that does not flow and that does not chase, with good slippery properties and a freshness sensation.

The deposit is light, comfortable, shiny, and covering. It is not tacky and procures a persistent moisturizing effect.

This composition is stable for one month and two months, at several temperatures: 20° C., 4° C., and 45° C.

The invention claimed is:

1. A composition in the form of a water-in-oil emulsion, containing:
    from 6% to 40% by weight in relation to the total weight of the composition, of at least one non-volatile hydrocarbon-based oil H1 chosen from plant oils with a molecular weight greater than 400 Da and non-volatile triglycerides with a molecular weight greater than 400 Da, non-volatile non-polar hydrocarbon-based oils with a molecular weight greater than 350 Da, non-volatile ester oils with a molecular weight greater than 350 Da, and mixtures thereof;
    optionally less than 5% by weight in relation to the total weight of said composition of non-volatile hydrocarbon-based oil(s) H2 chosen from non-volatile triglycerides with a molecular weight less than or equal to 400 Da; non-volatile ester oils with a molecular weight less than or equal to 350 Da; non-volatile non-polar hydrocarbon-based oils with a molecular weight less than or equal to 350 Da; dialkyl carbonates; and mixtures thereof;
    less than 1% of $C_{10}$-$C_{26}$ alcohols; if the composition contains any of the $C_{10}$-$C_{26}$ alcohols;
    from 15% to 70% by weight of water with respect to the total weight of said composition;
    ethylcellulose;
    at least one volatile hydrocarbon-based oil, a volatile silicon oil or mixtures thereof, with a content between 1% and 8%, by weight, in relation to the weight of the composition;
    at least one nonionic hydrocarbon-based or silicone surfactant; and
    from 0.5% to 15% by weight of at least one polar hydrocarbon-based wax chosen from beeswaxes; synthetic beeswaxes; (poly)oxyalkylenated hydrocarbon waxes, the oxyalkykenated pattern(s) being C2-C4 and (poly)glycerolated; alcohol waxes, and mixtures thereof, in relation to the weight of the composition.

2. The composition according to claim 1, wherein the polar hydrocarbon-based wax content ranges from 0.5% to 15% 2% to 10% by weight with respect to the total weight of said composition.

3. The composition according to claim 1, wherein the polar hydrocarbon-based wax is chosen from beeswax, synthetic beeswaxes, (poly)oxyalkylenated and (poly)glycerolated hydrocarbon waxes and mixtures thereof; waxes corresponding to partial or total esters of a saturated C16-C30 carboxylic acid, optionally hydroxylated, with glycerol; and
    mixtures thereof.

4. The composition according to claim 1, wherein the non-volatile hydrocarbon-based oil(s) H1 content ranges from 8% to 30% by weight with respect to the total weight of said composition.

5. The composition according to claim 1, which comprises, as non-volatile hydrocarbon-based oil(s) H1, at least one hydrocarbon-based plant oil and optionally at least one non-volatile non-polar hydrocarbon-based oil chosen from linear and branched hydrocarbons.

6. The composition according to claim 1, which comprises one or several non-volatile hydrocarbon-based oil(s) H2 chosen from C10-C26 monoalcohols, non-volatile triglycerides with a molecular weight less than or equal to 400 Da; non-volatile ester oils with a molecular weight less than or equal to 350 Da; non-volatile non-polar hydrocarbon-based oils with a molecular weight less than or equal to 350 Da, and mixtures thereof.

7. The composition according to claim 1, wherein the non-volatile hydrocarbon-based oil(s) H2 content is less than 3% by weight with respect to the total weight of said composition.

8. The composition according to claim 1, comprising from 20% to 60% by weight of water with respect to the total weight of the composition.

9. The composition according to claim 1, further comprising at least one non-volatile silicone oil, chosen from polydimethylsiloxanes and non-volatile phenylated silicone oils that do not have any dimethicone fragment, and mixtures thereof.

10. The composition according to claim 1, wherein the content in the at least one non-volatile silicone oil is between 2% and 10% by weight with respect to the weight of the composition.

11. The composition according to claim 1 further comprising at least one volatile hydrocarbon-based oil, a volatile silicone oil or mixtures thereof.

12. The composition according to claim 1 further comprising at least one pasty fat.

13. The composition according to claim 1, which comprises at least one additional wax.

14. The composition according to claim 1, wherein the content of the at least one additional wax is such that the at least one polar hydrocarbon-based wax/at least one additional wax weight ratio is greater than 1.

15. The composition according to claim 1, wherein the content of the at least one additional wax is less than or equal to 5% by weight by weight with respect to the total weight of said composition.

16. The composition according to claim 1, further comprising alkylcellulose, of which the alkyl portion is C2-C6.

17. The composition according to claim 1, further comprising a humectant or moisturizing agent.

18. The composition according to claim 1, comprising at least one non-ionic hydrocarbon-based or silicone surfactant, with an HLB less than or equal to 8.

19. The composition according to claim 1, further comprising at least one non-ionic hydrocarbon-based surfactant.

20. The composition according to claim 1, wherein the at least one surfactant content ranges from 2% to 10% by weight, with respect to the total weight of said composition.

21. A method for treating lips, comprising a step for applying on lips a composition according to claim 1.

* * * * *